(12) United States Patent
Thurston et al.

(10) Patent No.: US 6,909,006 B1
(45) Date of Patent: Jun. 21, 2005

(54) CYCLOPROPYLINDOLE DERIVATIVES

(75) Inventors: David Edwin Thurston, London (GB); Philip Wilson Howard, London (GB)

(73) Assignee: Spirogen Limited, Isle of Wight (GB)

(*) Notice: Subject to any disclaimer, the term of this patent is extended or adjusted under 35 U.S.C. 154(b) by 86 days.

(21) Appl. No.: 10/069,202

(22) PCT Filed: Feb. 22, 2000

(86) PCT No.: PCT/GB00/03291

§ 371 (c)(1),
(2), (4) Date: Feb. 22, 2002

(87) PCT Pub. No.: WO01/16104

PCT Pub. Date: Mar. 8, 2001

(30) Foreign Application Priority Data

Aug. 27, 1999 (GB) ............................. 9920427
Mar. 8, 2000 (GB) ............................. 0005576

(51) Int. Cl.⁷ ..................... C07D 209/60; C07D 209/96
(52) U.S. Cl. ..................... 548/427; 548/433; 548/450
(58) Field of Search ................. 548/427, 433, 548/450

(56) References Cited

U.S. PATENT DOCUMENTS

| | | | |
|---|---|---|---|
| 3,523,941 A | 8/1970 | Leimgruber et al. | 260/239.3 |
| 3,524,849 A | 8/1970 | Batcho et al. | 260/239.3 |
| 4,239,683 A | 12/1980 | Takanabe et al. | 260/239.3 |
| 4,309,437 A | 1/1982 | Ueda et al. | 424/274 |
| 5,143,854 A | 9/1992 | Pirrung et al. | 436/518 |
| 5,545,568 A | 8/1996 | Ellman | 436/518 |

FOREIGN PATENT DOCUMENTS

| | | |
|---|---|---|
| FR | 2 586 683 | 3/1987 |
| GB | 1 299 198 | 12/1972 |
| JP | 57-131791 | 8/1982 |
| JP | 58180487 A | 10/1983 |
| WO | WO 88/04659 | 6/1988 |
| WO | WO 91/16324 | 10/1991 |
| WO | WO 92/19620 | 11/1992 |
| WO | WO 96/23947 | 8/1996 |
| WO | WO 97/01560 | 1/1997 |
| WO | WO 97/07097 | 2/1997 |
| WO | WO 98/11101 | 3/1998 |
| WO | WO 98/12197 | * 3/1998 |
| WO | WO 99/29642 | 6/1999 |
| WO | WO 00/12506 | 3/2000 |

OTHER PUBLICATIONS

Boger et al. Journal of the American Chemical Society (1992), 114(25), 10056–8.*
Althuis, T.H. et al., "Synthesis and identification of the major metabolites of Prazosin formed in dog and rat," 20:1, 146–149 (1977).
Aristoff, P.A. et al., "Synthesis of CBI–PDE–I–Dimer, the benzannelated analogue of CC–1065," J.Org.Chem., 57, 6234–6239 (1992).

Aristoff, P.A. et al., "Synthesis of biochemical evaluation of the CBI–PDE–I–dimer, a benzannelated analog of (+)–CC–1065 that also produces delayed toxicity in mice," J.Med.Chem., 36, 1956–1963 (1993).

Baraldi, P.G. et al., "Design, synthesis and biological activity of a pyrrolo [2,I-c][1,4] benzodiazepine (PBD)–distamycin hybrid," Bioorg. Med. Chem. Ltrs., 8, 3019–3024 (1998).

Bi, Y. et al, "Building blocks for peptide and carbamate libraries," Bioorg. Med. Chem. Ltrs, 6:19, 2299–2300 (1996).

(Continued)

*Primary Examiner*—Bruck Kifle
(74) *Attorney, Agent, or Firm*—Michael Best & Friedrich LLP

(57) ABSTRACT

Compounds of formula (III) or (V), wherein is a solid support; L is a linking group or a single bond; T is a combinatorial unit; n is a positive integer, where if n is greater than 1, each T may be different: X is an electrophilic leaving group; Y is selected from NH-Prot, O-Prot, S-Prot, $NO_2$, —NHOH. $N_3$, NHR, NRR, N=NR, N(O)RR, $NHSO_2R$, N=N=PhR, SR or SSR, where Prot represents a protecting group; A and B collectively represent a fused benzene or pyrrole ring (in either orientation), which is optionally substituted by up to respectively 4 or 2 groups independently selected from R, OH, OR, halo, nitro, amino, $Me_3Sn$, $CO_2H$, $CO_2R$, $R_1$ is a nitrogen protecting group, where if Y includes a protecting group, these protecting groups are orthogonal and $R_2$ and $R_7$ are independently selected from H, R, OH, OR, halo, nitro, amino, $Me_3Sn$, and other related compounds and collections of compounds.

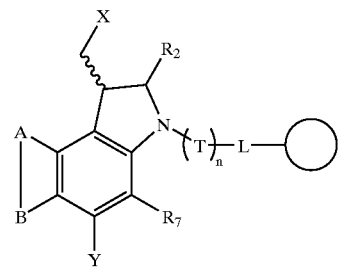

(III)

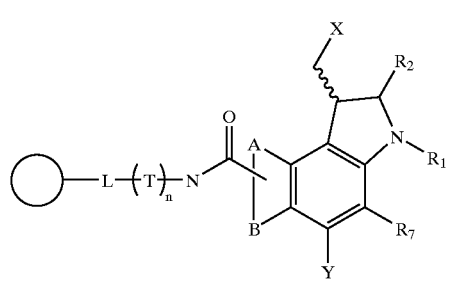

(V)

10 Claims, No Drawings

OTHER PUBLICATIONS

Bi, Y., et al, "Building blocks for peptide and carbamate libraries," *Chemical Abstracts*, 300965y, 125:23, p. 1013 (1996).

Boger, D.L., "Design, synthesis, and evaluation of DNA minor groove binding agents: the duocarmycins," *Pure & Appl. Chem.*, 66:4, 837–844 (1994).

Boger, D.L. et al., "Total synthesis and evaluation of ±–N–(tert–butyloxycarbonyl)–CBI (±)–CBI–CDPI$_1$, and (±)–CBI–CDPI$_2$ CC–1065 functional agents incorporating the equivalent 1,2,9,9a–tetrahydrocycloprop[1,2–c]benz[1,2–e]indol–4–one(CBI) left–hand subunit," *J. Am. Chem Soc.*, 111:16, 6461–6453 (1989).

Boger, D.L. et al., "Synthesis of N–(tert–butyloxycarbonyl)–CBI,CBI,CBI–CDPI$_I$, and CBI–CDPI$_2$: Enhanced functional analogues of CC–1065 incorporating the 1,2,9,9a–tetrahydrocyclopropa[c]benz[e]indol–4–one (CBI) left–hand subunit,". *Org. Chem.*, 55:23, 5823–5832 (1990).

Boger, D.L. et al., "An efficient synthesis of 1,2,9,9a–tetrahydrocyclopropa[c]benz[e] indol–4–one (CBI): An enhanced and simplified analog of the CC–1065 and duocarmycin alkylation subunits," *J. Org. Chem.*, 60:5, 1271–1275 (1995).

Boger, D.L. et al., "CBI–TMI: Synthesis and evaluation of a key analog of the duocarmycins. Validation of a direct relationship between chemical solvolytic stability and cytotoxic potency and confirmation of the structural features responisble for the distinguishing behavior of enantiomeric paris of agents," *J. Am. Chem. Soc.*, 116:18, 7996–8006 (1994).

Boger, D.L. et al., "CC–1065 and the duocarmycins: synthetic studies," *Chem. Rev.*, 97:3, 787–828 (1997).

Bose, D.S et al., "New approaches to pyrrolo[2,1–c][1,4] benzodiazepines: synthesis, DNA–binding and cytotoxicity of DC–81," *Tetrahedron*, 48:4, 751–758 (1992).

Bose, D.S. et al., "Rational design of a highly efficient irreversible DNA interstrand cross–linking agent based on the pyrrolobenzodiazepine ring system," J. am. Chem. Soc., 114:12, 4939–4941 (1992).

Brown, S.C. et al., "NMR solution structure of a peptide nucleic acid complexed with RNA," *Science*, 265, 777–780 (1994).

Burgess, K. et al., "Solid phase syntheses of oligoureas," *J. Am. Chem. Soc.*, 119:7, 1556–1564 (1997).

Burgess, K. et al., "Solid–phase syntheses of unnatural biopolymers containing repeating urea units,"*Agnew. Chem. Int. Ed. Engl.*, 34:8, 907–909 (1995).

Cava, M.P. & Drost, K.J., "a photochemically based synthesis of the benzannelated analogue of the CC–1065 A unit," *J. Org. Chem.*, 56:6, 2240–2244 (1991).

Cho, C.Y. et al., "An unnatural biopolymer," *Science*, 261, 1303–1305 (1993).

Courtney, S.M. et al., "A new convenient procedure for the synthesis of pyrrolo[2,1–c][1,4]benzodiazepines," *Tetrahedron Ltrs.*, 34:33, 5327–5328 (1993).

Edman, P. et al., "A protein sequenator," *European J. Biochem.*, 1:1, 80–91 (1967).

Egholm, M. et al., "Peptide nucleic acids (PNA). Oligonucleotide analogues with an achiral peptide backbone," *J. Am. Chem. Soc.*, 114, 1895–1897 (1992).

Egholm, M. et al., "PNA hybridizes to complementary oligonucleotides obeying the Watson–Crick hydrogen–bonding rules," *Nature*, 365, 566–568 (1993).

Farmer, J.D., Jr. et al., "DNA binding properties of a new class of linked anthramycin analogs," *Chemical Abstract*, 239940r, 114:25, p. 25 (1991).

Figliozzi, G.M. et al., "Synthesis of N–substituted glycine peptoid libraries," *Methods in Enzymology*, 267:25 437–47 (1996).

Foloppe, M.P. et al., "DNA–binding properties of pyrrolo [2,1–c][1,4]–benzodiazepine N10–C11 amidines," *Eur. J. Med. Chem.*, 31, 407–410 (1996).

Fujisawa Pharm., "Benzodiazepine derivatives," *Chemical Abstracts*, 139983k, 99:17, 603 (1983).

Fujisawa Pharm., "Benzodiazepine derivatives," *Chemical Abstracts*, 72145x, 98:9, 638 (1983).

Fukuyama, T. et al., "Total synthesis of (+)–porothramycin B," *Tetrahedron Ltrs.*, 34:16, 2577–80 (1993).

Furka, A. et al., "General method for rapid synthesis of multicomponent peptide mixtures," *In. J. Peptide Protein Res.*, 37 487–493 (1991).

Gregson, S.J. et al., "Synthesis of a novel C2/C2'–exo unsaturated pyrrolobenzodiazepine cross–linking agent with remarkable DNA binding affinity and cytotoxicity," *Chem. Commun.*, 797–798 (1999).

Guiotto, A. et al., "Synthesis of novel C7–aryl substituted pyrrolo[2,1–c][1,4]benzodiazepines (PBDs) via pro–N10–troc protection and suzuki coupling," *Bioorg. Med. Chem. Ltrs.*, 8:21, 3017–3018 (1998).

Hara, M. et al., "A new glycosidic pyrrolo[1,4]benzodiazepine antibiotic produced by *Streptomyces* sp." *J. Antibiotics*, 41:5, 702–704 (1988).

Hochlowski, J.E. et al., "Abbeymycin, a new anthramycin–type antibiotic produced by a *Streptomycete,*" *J. of Antibiotics*, 40:2, 145–148 (1987).

Hurley, L.H. et al., "Covalent binding of antitumor antibiotics in the minor groove of DNA. Mechanism of action of CC–1065 and the pyrrolo[1,4]benzodiazepines,"*Acc. Chem. Res.*, 19, 230–237 (1986).

Itoh, J. et al., "Sibanomicin, a new pyrrolo[1,4]benzodiazepine antitumor antibiotic produced by a *Micromonospora* sp.," *J. Antibiotics*, 41:9, 1280–1284 (1988).

Jenkins, T.C. et al., "Structure of a covalent DNA minor groove adduct with a pyrrolobenzodiazepine dimer: Evidence for sequence–specific interstrand cross–linking," *J. Med. Chem.*, 37:26, 4529–4537 (1994).

Kohn, K.W., "Anthramycin," *Antibiotics, III*, 3–11 (1975).

Konishi, M. et al., "Chicamycin, a new antitumor antibiotic II. Structure determination of chicamycins A and B," *J. Antibiotics*, 37:3, 200–206 (1984).

Kunimoto, S. et al., "Mazethramycin, a new member of anthramycin group antibiotics," *J. Antibiotics*, 33:6, 665–667 (1980).

Langley, D.R. et al., "A versatile and efficient synthesis of carbinolamine–containing pyrrolo[1,4]benzodiazepines via the cyclization of N–(2–aminobenzoyl)pyrrolidine–2carboxaldehyde diethyl thioacetals: Total synthesis of prothracarcin," *J. Organ. Chem.*, 52:1, 91–97 (1987).

Leber, J.D. et al., "A revised structure for sibiromycin," *J. Am. Chem. Soc.*, 100:9, 2992–2993 (1988).

Leimgruber, M. et al., "The structure of anthramycin," *J. Am. Chem. Soc.*, 87:24, 5793–5795 (1965).

Leimbruger, M. et al., "Isolation and characterization of anthramycin, a new antitumor antibiotic," *J. Am. Chem. Soc.*, 87:24, 5791–5793 (1965).

Lescrinier, T. et al., "DNA–binding ligands from peptide libraries containing unnatural amino acids," *Chem. Eur. J.*, 4:3, 425–433 (1998).

Lown, J.W. et al., "Antitumor antibiotics," *Biochem. Pharmacol.*, 28:13, 2017–2026 (1979).

Monks, A. et al., "Feasibility of a high–flux anticancer drug screen using a diverse panel of cultured human tumor cell lines," *J. of Nat'l Cancer Inst.*, 83:11, 757–765 (1991).

Moran, E.J. et al., "Novel biopolymers for drug discovery," *Peptide Science*, 37, 213–219 (1995).

Nagasaka, T. et al., "Stereoselective synthesis of tilivalline," *Tetrahedron Letters*, 30:14, 1871–1872 (1989).

Nagasaka, T. et al., "Stereoselective synthesis of tilivalline," *J. Org. Chem.*, 63:20, 6797–6801 (1998).

Nielsen, P.E. et al., "Sequence–selective recognition of DNA by strand displacement with a thymine–substituted polyamide," *Science*, 254, 1497–1500 (1991).

O'Neil, Ian et al., "The synthesis of functionalized pyrrolo [2,1–e][1,4]–benzodiazepines," *Chemical Abstracts*, 126:13, 618 (1997) and entire article.

O'Neil, Ian A. et al., "DPPE: A convenient replacement for triphenylphosphine in the Staudinger and Mitsunobu reactions," *Tetrahedron Letters*, 39:42, 7787–7790 (1998).

Paikoff, S.J. et al., "The solid phase synthesis of N–alkylcarbamate oligomers," *Tetrahedron Letters*, 37:32, 5653–5656 (1996).

Rawal, V.H. et al., Photocyclization stategy for the synthesis of antitumor agent CC–1065: Synthesis of dideoxy PDE–I and PDE–II. Synthesis of Thiophene and Furan analogues of dideoxy PDE–I and PDE–II, *J. Org. Chem.*, 52:1, 19–28 (1987).

Reynolds, V.L. et al., "The chemistry, mechanism of action and biological properties of CC–1065, a potent antitumor antibiotic," *J. Antibiotics*, 39:3, 319–334 (1986).

Saha, A.K. et al., "Diisopropylsilyl–linked oligonucleotide analogs: Solid–phase synthesis and physicochemical properties," *J. Org. Chem.*, 58:27, 7827–7831 (1993).

Schreiber, S.L., Kapoor, T.M. et al., "Exploring the specificity pockets of two homologous SH3 domains using structure–based, split–pool synthesis and affinity–based selection," *J. Am. Chem. Soc.*, 120:1, 23–29 (1998).

Shimizu, K. et al., "Prothracarcin, a novel antitumor antibiotic," *J. Antibiotics*, 35:8, 972–978 (1982).

Simon, R.J. et al., "Peptoids: A modular approach to drug discovery," *Proc. Natl. Acad. Sci. USA*, 89, 9367–9371 (1992).

Soth, M.J. et al., "Unnatural oligomers and unnatural oligomer libraries," *Curr. Opin. Chem. Biol.*, 1:1, 120–129 (1997).

Takeuchi, T. et al., "Neothramycins A and B, new antitumor antibiotics," *J. Antibiotics*, 29:1, 93–96 (1976).

Thurston, D.E. et al., "Synthesis of DNA–interactive pyrrolo [2,1–c][1,4]benzodiazepines," *Chem. Rev.* 94:2, 433–465 (1994).

Thurston, D.E. et al., "The molecular recognition of DNA," *Chem. Britain*, 26, 767–772 (1990).

Thurston, D.E. et al., "Synthesis of a novel GC–specific covalent–binding DNA affinity–cleavage agent based on pyrrolobenzodiazepines (PBDs)," *Chem. Commun.*, 563–565 (1996).

Thurston, D.E., "Advances in the study of pyrrolo[2,1–c] [1,4]benzodiazepine (PBD) antitumor antibiotics," *Molecular Aspects of Anticancer Drug–DNA Interaction*, Neidle, S., Waring, M.J., Eds.; Macmillan Press Ltd., v.1, 54–88 (1993).

Thurston, D.E. et al., "Effect of A–ring modifications on the DNA–binding behavior and cytotoxicity of pyrrolo[2,1–c], [1,4]benzodiazepines," *J. Med. Chem.* 42:11, 1951–1964 (1999).

Tsunakawa, M. et al., "Porothramycin, a new antibiotic of the anthramycin group: production, isolation, structure and biological activity," *J. Antibiotics*, 41:10, 1366–1373 (1988).

Umezawa, H. et al., "Mazethramycins," *Chemical Abstracts*, 90:1, 428 (1979).

Wilson, S.C., et al., "Design and Synthesis of a novel epoxide–containing pyrrolo[2,1–c][1,4]benzodiazepine (PBD) via a new cyclization procedure," *Tetrahedron Ltrs.*, 36:35, 6333–6336 (1995).

Zuckermann, R.N. et al., "Discovery of nanomolar ligands for 7–transmembrane G–protein–coupled receptors from a diverse N–(substituted)blycine peptoid library," *J. Med. Chem.*, 37:17, 2678–2685 (1994).

\* cited by examiner

CYCLOPROPYLINDOLE DERIVATIVES

CROSS REFERENCE TO RELATED APPLICATIONS

This patent application is a national stage filing under 35 U.S.C. 371 of International Application No. PCT/GB00/03291, filed on Aug. 24, 2000, which claims benefit to Great Britain Application No. 0005576.4, filed on Mar. 8, 2000, and Great Britain Application No. 9920427.3, filed on Aug. 27, 1999.

1. Technical Field

This invention relates to cyclopropylindoles (CPI) (which term is used to encompass cyclopropylbenzindoles (CBI)) compounds and their precursors, to methods of synthesizing these compounds on solid supports, and to compounds of utility therein. This invention further relates to collections of these compounds, and methods for identifying and isolating CPI and precursor compounds with useful and diverse activities from such collections.

2. Background to the Invention

A large number of both synthetic and naturally occurring low molecular weight ligands are known that interact with DNA via a number of different mechanisms, including covalent or non-covalent interaction in the minor or major grooves, intercalation between base pairs or other types of non-specific interactions.

Of the class of ligands which interact with the minor groove, GC specific ligands include Chromomycin, pyrrolo[2,1-c][1,4]benzodiazepines (PBDS), Mitomycins and Ecteinascidins. Of these, all but Chromomycin form a covalent bond with the DNA. Of AT specific ligands, cyclopropylindoles form covalent bonds, whilst compounds such as distamycin and netropsin do not.

Cyclopropylindole (CPI) compounds are a class of highly potent antitumour antibiotics which includes the natural products CC-1065 (V. L. Reynolds et al, J. Antibiot., 39, 1986, 319–314) and the duocarmycins (D. L. Boger, Pure & Appl. Chem., 66, 1994, 837–844), having $IC_{50}$s in the low pM range in tumour cells growing in vitro. They are of the general structures A and B:

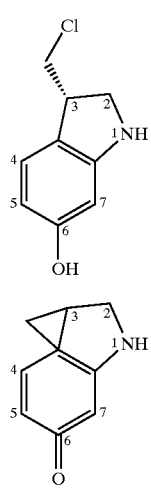

Studies with compounds that model the binding subunit have shown that the more stable open chain seco-precursors (e.g. A) are as potent as the cyclopropylindole compounds (e.g. B). Further, ring closure is not essential for DNA binding.

A number of synthetic analogues of the natural products have been prepared in which the oxygen of A is protected as a carbamate that must be cleaved (by non-specific enzymatic hydrolysis) for activity. Further analogues of a similar type are disclosed in WO88/04659 and WO91/16324. Analogues where the 6 substituent is N or S are disclosed in WO 97/07097 and WO 98/11101.

Compounds having biological activity can be identified by screening collections of compounds (i.e. libraries of compounds) produced through synthetic chemical techniques. Such screening methods include methods wherein the library comprises a plurality of compounds synthesized at specific locations on the surface of a solid support where a receptor is appropriately labelled to identify binding to the compound, e.g., fluorescent or radioactive labels. Correlation of the labelled receptor bound to the support with its location on the support identifies the binding compound (U.S. Pat. No. 5,143,854).

Central to these methods is the screening of a multiplicity of compounds in the library and the ability to identify the structures of the compounds which have a requisite biological activity. In order to facilitate synthesis and identification, the compounds in the library are typically formed on solid supports. Usually each such compound is covalently attached to the support via a cleavable or non-cleavable linking arm. The libraries of compounds can be screened either on the solid support or as cleaved products to identify compounds having good biological activity.

3. Disclosure of the Invention

The present invention provides CPI compounds with structures that allow them to be joined to combinatorial chains, as well as combinatorial libraries containing CPIs themselves.

A first aspect of the present invention relates to compounds of formula I:

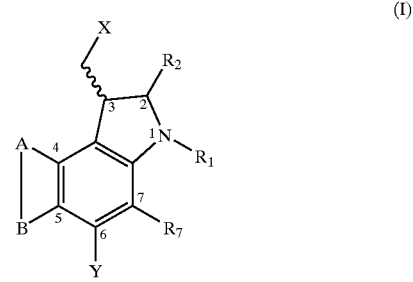

wherein X is an electrophilic leaving group;

Y is selected from NH-Prot, O-Prot, S-Prot, $NO_2$, NHOH, $N_3$, NHR, NRR, N=NR, N(O)RR, $NHSO_2R$, N=NPHR, SR or SSR, where Prot represents a protecting group;

A and B collectively represent a fused benzene or pyrrole ring (in either orientation), which is optionally substituted by up to respectively 4 or 2 groups independently selected from R, OH, OR, halo, nitro, amino, $Me_3Sn$, $CO_2H$, $CO_2R$;

$R_1$ is a nitrogen protecting group, where if Y includes a protecting group, these protecting groups are orthogonal;

$R_2$ and $R_7$ are independently selected from H, R, OH, OR, halo, nitro, amino, $Me_3Sn$; wherein R is selected from
(a) a lower alkyl group having 1 to 10 carbon atoms,
(b) an aralkyl group (i.e. an alkyl group with one or more aryl substituents), preferably of up to 12 carbon atoms; the alkyl group of (a) or (b) optionally containing one or more carbon—carbon double or triple bonds, which may form part of a conjugated system; and (c) an aryl group, preferably of up to 12 carbon atoms; and wherein R is optionally substituted by one or more halo, hydroxy, amino, or nitro groups, and optionally contains one or more hetero atoms, which may form part of, or be, a functional group; except that when $R_1$ is Boc, Y is $NO_2$, X is Cl, and $R_2$ and $R_7$ are H, then A and B do not collectively represent either an unsubstituted benzene ring or:

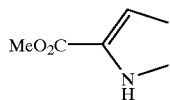

If R is an aryl group, and contains a hetero atom, then R is a heterocyclic group. If R is an alkyl chain, and contains a hetero atom, the hetero atom may be located anywhere in the alkyl chain, e.g. —O—$C_2H_5$, —$CH_2$—S—$CH_3$, or may form part of, or be, a functional group, e.g. carbonyl, hydroxy.

R is preferably independently selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups. It is more preferred that R is independently selected from lower alkyl groups having 1 to 10 carbon atoms optionally substituted by one or more halo, hydroxy, amino, or nitro groups. It is particularly preferred that R is an unsubstituted straight or branched chain alkyl group, having 1 to 10, preferably 1 to 6, and more preferably 1 to 4, carbon atoms, e.g. methyl, ethyl, propyl, butyl.

Y is preferably NH-Prot, O-Prot, S-Prot, and more preferably NH-Prot.

These compounds are useful in the synthesis of collections of CBI and CPI precursors. Compounds of formula I:

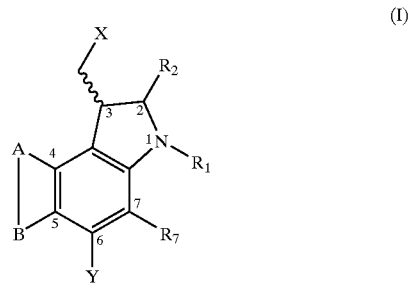

(I)

wherein X A, B, $R_1$, $R_2$, $R_7$ are as defined above and Y is selected from $NH_2$, NH-Prot, OH, O-Prot, SH, S-Prot, $NO_2$, NHOH, $N_3$, NHR, NRR, N=NR, N(O)RR, $NHSO_2R$, N=NPhR, SR or SSR, where Prot represents a protecting group can be attached to a solid support, e.g. via a connecting link which may comprise a chain of combinatorial units. This is a second aspect of the invention, i.e. the use of these compounds in methods of combinatorial chemistry synthesis, wherein the compound is joined to a solid support by a chain comprising at least one combinatorial unit. The preferences for R expressed in the first aspect apply to this aspect of the invention.

Y in this second aspect is preferably $NH_2$, NH-Prot, OH, O-Prot, SH, S-Prot, more preferably $NH_2$ NH-Prot, SH, S-Prot, and most preferably NH-Prot. As an alternative, OH and O-Prot are preferred.

Furthermore, compounds of formula (I) with substituents as defined in this aspect, where the fused ring, represented by -A-B-, bears a substituent —$CO_2H$ or —$CO_2R$, may be used as combinatorial units (see below).

The term 'protecting group' (and more specifically 'nitrogen protecting group') has the meaning usual in synthetic chemistry, particularly for 'nitrogen protecting group', in synthetic peptide chemistry. It means any group which may be covalently bound to the protected atom of the CBI or CPI grouping, and permits reactions to be carried out upon the molecule containing this grouping without its removal. Nevertheless, it is able to be removed from the protected atom without affecting the remainder of the molecule. Suitable nitrogen protecting groups for the present invention include Fmoc (9-fluorenylmethoxycarbonyl), Nvoc (6-nitroveratryloxycarbonyl), Teoc (2-trimethylsilylethyloxycarbonyl), Troc (2,2,2-trichloroethyloxycarbonyl), Boc (t-butyloxycarbonyl), CBZ (benzyloxycarbonyl), Alloc (allyloxycarbonyl) or Psec (2 (-phenylsulphonyl)ethyloxycarbonyl). Suitable oxygen (hydroxyl) protecting groups include t-butyl ethers, Benzyl ethers, Silyl ethers, MOM (methoxy methyl ethers), MEM (2-methoxy ethoxy methyl ethers) or acetates. Suitable sulphur (thiol) protecting groups include benzyl, nitrogenzyl thioether or fluorenylmethyl thioethers. Other suitable groups are described in Protective Groups in Organic Synthesis, T Green and P Wuts, published by Wiley, 1991, which is incorporated herein by reference.

In the first and second aspects of the invention it is preferred that the nitrogen protecting group has a carbamate functionality where it binds to the nitrogen atom to be protected.

The term 'orthogonal' in relation to 'protecting groups' has the meaning usual in synthetic chemistry. It means that one protecting group may be selectively removed without affecting the other protecting group. This is achieved by using protecting groups which are sensitive to different removal conditions.

Examples of orthogonal protecting group pairs are:
CBZ carbamate and Boc Carbamate—the CBZ group can be removed by hydrogenation whilst the BOC carbamate remains intact.

Alternatively, the BOC group can be removed with TFA whilst the CBZ group remains intact. The same applies to a CBZ carbamate and a tert-butyl ether.

Fmoc carbamate and t-butyl ether—The Fmoc group can be removed with base (50% piperidine in DMF) without affecting the t-butyl protection. The t-butyl side chain protecting group is removed by acid (TFA, trifluoroacetic acid). If necessary t-butyl ethers can be cleaved in the presence of Fmoc as Fmoc is unaffected by acid. Alloc carbamate and Silyl ethers—an allyl carbamate is cleaved specifically by zero valent palladium catalysts, Silyl ethers are cleaved with fluoride ions or dilute acid (neither reagent affects Alloc and palladium does not affect Silyl ethers).

An example of non-orthogonal pair includes CBZ and Fmoc, as both are cleaved by hydrogenation.

An electrophilic leaving group is a group that is readily eliminated from the molecule and carries with it an electron-pair. These may be termed "nucleogufugal" leaning groups.

In the present invention, it is preferred that X is either halogen or $OSO_2R$, where R is as defined earlier. A halogen group means a fluoro, chloro, bromo or iodo group. It is more preferred that X is Cl.

If X is $OSO_2R$, then R is preferably —$CH_3$(mesylate), -(p-Me)Ph (tosylate), —$CF_3$(triflate) or —$C_4F_9$(nonaflate)

In the present invention it is also further preferred that the 4,5 fused ring is substituted by —$CO_2R$ in the 2 or 3 position if it is a benzene ring, and the 2 position if it is a pyrrole ring, e.g.

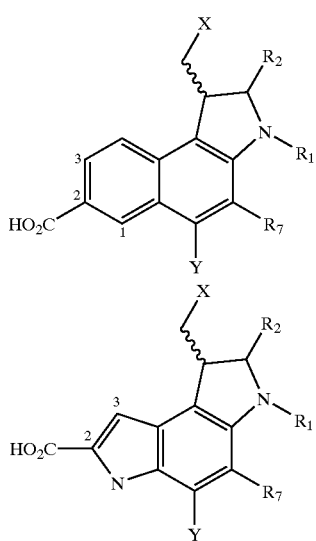

where $R_2$ and $R_7$ are preferably H, with the proviso that Y is not $NO_2$ when $R_1$ is Boc, $R_2$ and $R_7$ are H, and X is Cl.

A third aspect of the present invention relates to compounds of the formula III:

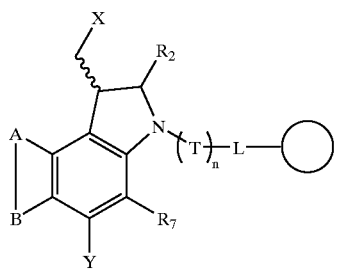

wherein X, Y, A, B, $R_2$ and $R_7$ are as defined in the second aspect;
T is a combinatorial unit;
and n is a positive integer, where if n is greater than 1, each T may be different;
L is a linking group, or less preferably a single bond;
and O is a solid support.

A fourth aspect of the present invention relates to compounds of formula III':

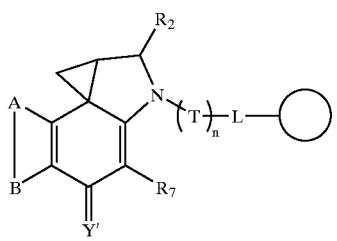

where A, B, $R_2$, $R_7$, T, n, L and O are as defined in the third aspect; and
Y' is NH, NR, O or S, preferably NH or S.

Compounds of this aspect are obtainable from compounds of the second aspect by removal of the protecting group preferably carbamate in Y (if present), or by other appropriate reactions, e.g. reduction and/or basic conditions. The cyclisation may also occur spontaneously. A fifth aspect of the present invention relates to compounds of formula II:

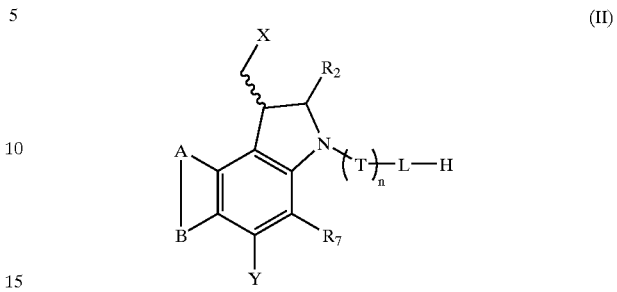

wherein X, Y, A, B, $R_2$, $R_7$, T and n are as defined in the third aspect of the invention.

Compounds of this aspect are obtainable by cleavage of the linking group of the appropriate compound of the third aspect.

A sixth aspect of the present invention relates to compounds of the formula II':

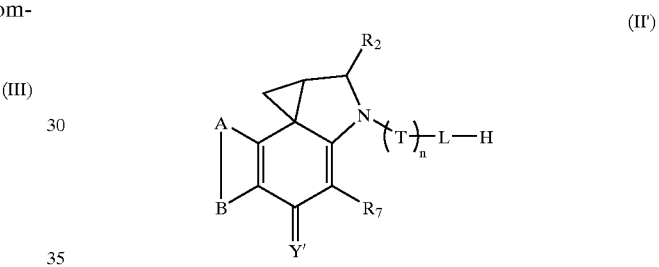

wherein A, B, T, n, $R_2$ and $R_7$ are as defined in the fifth aspect of the invention; and
Y' is NH, NR, O, or S, preferably NH or S.

Compounds of this aspect are obtainable by cleavage of the linking group of the appropriate compound of the third aspect (see below). Alternatively, they are obtainable from compounds of the fourth aspect by removal of the protecting group in Y (if present), or by other appropriate reactions, e.g. reduction and/or basic conditions. The cyclisation may also occur spontaneously.

A seventh aspect of the present invention relates to compounds of formula V:

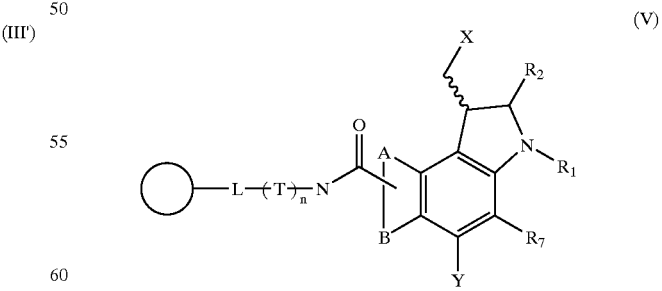

where A, B, Y, $R_1$, $R_2$, $R_7$, and X are defined in the second aspect of the invention, and T, n, L and O are as defined in the third aspect of the present invention.

An eighth aspect of the present invention relates to compounds of formula V':

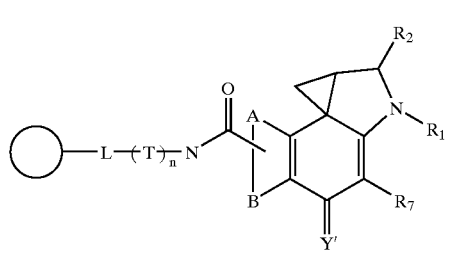
(V')

where A, B, $R_1$, $R_2$, $R_7$, T, n, L and O are as defined in the seventh aspect; and
Y' is NH, NR, O or S, preferably NH or S.

Compounds of this aspect are obtainable from compounds of the seventh aspect by removal of the protecting group in Y (if present), or by other appropriate reactions, e.g. reduction and/or basic conditions. The cyclisation may also occur spontaneously.

A ninth aspect of the present invention relates to compounds of formula IV:

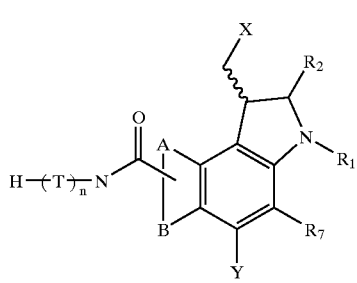
(IV)

wherein A, B, X, Y, T, n, $R_1$, $R_2$ and $R_7$ are as defined in the seventh aspect of the invention.

Compounds of this aspect are obtainable by cleavage of the linking group of the appropriate compound of the seventh aspect.

A tenth aspect of the present invention relates to compounds of formula IV':

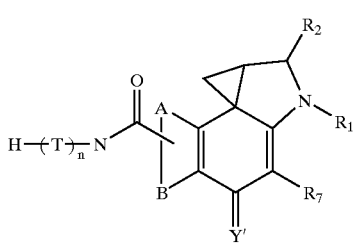
(IV')

wherein A, B, T, n, $R_1$, $R_2$ and $R_7$ are as defined in the ninth aspect of the invention; and
Y' is NH, NR, O, or S, preferably NH or S.

Compounds of this aspect are obtainable by cleavage of the linking group of the appropriate compound of the eighth aspect (see below). Alternatively, they are obtainable from compounds of the ninth aspect by removal of the protecting group in Y (if present), or by other appropriate reactions, e.g. by reduction and/or basic conditions. The cyclisation may also occur spontaneously.

An eleventh aspect of the invention is the preparation of compounds according to either the third or seventh aspects by reaction of a compound of formula VI:

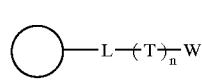
(VI)

with a compound of formula I according to the second aspect, where T, n, L and O are as defined in these aspects, and W is H or an atom or group for providing a functional group capable of reaction with —COOH or —$NH_2$. This reaction will include the necessary protection and deprotection steps so as to selectively achieve a compound according to the third or seventh aspect.

A twelfth aspect of the invention relates to compounds of formula VII:

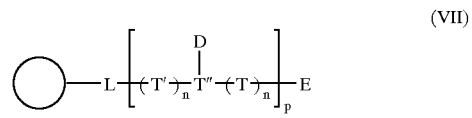
(VII)

wherein:
O, T, and L are as defined in the third aspect of the invention;
n and m are positive integers, or one of them may be zero;
T' is a combinatorial unit, where each T' may be different if m is greater than 1;
T'' is a combinatorial unit which provides a site for the attachment of D;
D is selected from:

(a)

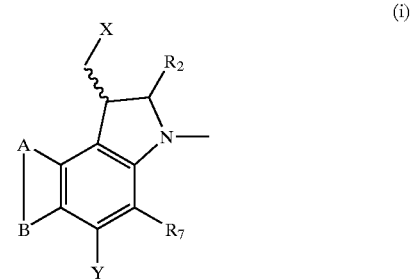
(i)

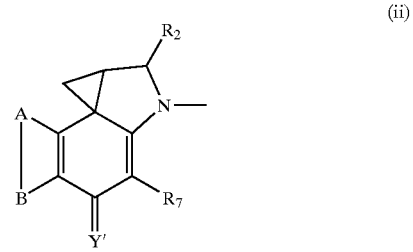
(ii)

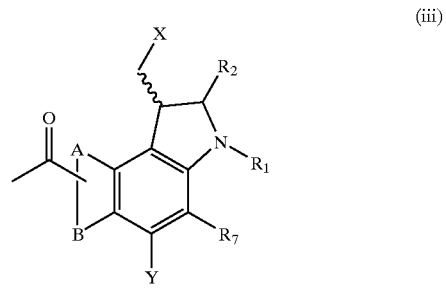
(iii)

-continued (iv)

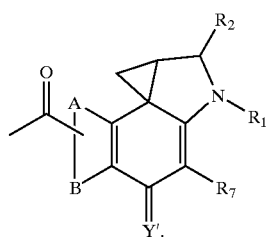

wherein A, B, Y, Y, R₂ and R₇ are as defined in the second or third aspects of the invention; or (b)

(i)

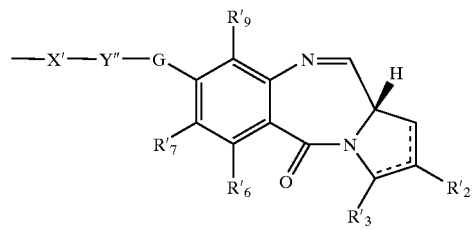

(ii)

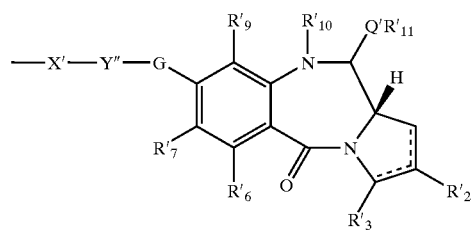

wherein X' is selected from CO, NH, S, or O;

G is O, S, NH, or a single bond;

R'₂ and R'₃ are independently selected from: H, R, OH, OR, =O, =CH—R'=CH₂, CH₂—CO₂R, CH₂—CO₂H, CH₂—SO₂R, O—SO₂R, CO₂R, COR and CN, and there is optionally a double bond between C₂ and C₃;

R'₆, R'₇, and R'₉ are independently selected from H, R, OH, OR, halo, nitro, amino, Me₃Sn;

R'₁₁ is either H or R;

Q' is S, O or NH;

R'₁₀ is a nitrogen protecting group;

Y" is a divalent group such that HY=R;

p is a positive integer, where if p is greater than 1, for each repeating unit, the meaning of T, T', T" and D and the values of n and m are independently selected; and E is selected from the same possibilities as D, provided that at least one group D or E is selected from (a).

If, for example, D terminates with CO then the site on T" may be NH, and if D terminates with NH, S or O, then the site on T" may be CO.

In preferred embodiments of this aspect, one of D and E is selected from (a) and the other is selected from (b).

A thirteenth aspect of the invention relates to compounds of formula (VIII):

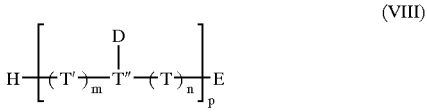

(VIII)

wherein L, T, T', T", D, E, n, m and p are as defined in the twelfth aspect of the invention.

In preferred embodiments of this aspect, one of D and E is selected from (a) and the other is selected from (b)

A fourteenth aspect of the invention relates to compounds of formula (IX):

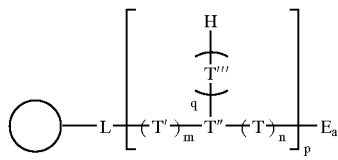

(IX)

wherein O, L, T, T', T", n, m and p are as defined in the twelfth aspect of the invention;

T''' is a combinatorial unit;

q is a positive integer, where if q is greater than 1, each T''' may be different; and $E_a$ is selected from the group (a) of E as defined in the twelfth aspect of the invention;

where if p is greater than 1, for each repeating unit the meaning of T, T', T", T''' and the values of n, m and q are independently selected.

A fifteenth aspect of the invention relates to compounds of formula (X):

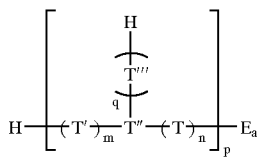

(X)

wherein L, T, T', T", T''', $E_a$, n, m, p and q are as defined in the fourteenth aspect of the invention.

It is recognised that the compounds of formulae I, II, II', III, III, IV, IV', V, V', VII, VIII, IX and X may exist in different enantiomeric or diastereomeric forms. In such cases it is to be understood that the above formulae represent any possible enantiomeric or diastereomeric form or a mixture thereof.

Solid Support

The term 'solid support' refers to a material having a rigid or semi-rigid surface which contains or can be derivatized to contain reactive functionalities which can serve for covalently linking a compound to the surface thereof. Such materials are well known in the art and include, by way of example, silicon dioxide supports containing reactive Si—OH groups, polyacrylamide supports, polystyrene supports, polyethyleneglycol supports, and the like. Such supports will preferably take the form of small beads, pins/crowns, laminar surfaces, pellets, disks. Other conventional forms may also be used.

Linker Group

The linking groups suitable for the present application are ones which usually provide in the structure:

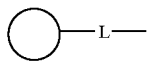

at least one covalent bond which can be readily broken by specific chemical reactions, such as oxidation (e.g. using DDQ or CAN), nucleophilic attack (e.g. with an amine on an oxime linker, or an alkylated sulfamyl linker (or by light, e.g. 365 nm, or changes in pH, e.g. by adding TFA) thereby providing for liberation of compounds free from the solid support. The methods employed to break the covalent bond are selected so as to be specific for the desired bond breakage thereby preventing unintended reactions from occurring elsewhere on the complex. The linking group is selected relative to the synthesis of the compounds to be formed on the solid support so as to prevent premature cleavage of this compound from the solid support as well as to limit interference by any of the procedures employed during compound synthesis on the support.

Examples of resins incorporating cleavable linking groups are set out in the table below, which also indicates the groups that can be immobilised thereon, along with the suggested cleavage methods for the linking group. Such resins are commercially available (e.g. from NovaBiochem).

| Linker/Resin Type | Immobilises | Cleavage Method |
|---|---|---|
| 2-Chlorotrityl chloride | $RNH_2$, $RCO_2H$, ROH, RSH | 1–50% TFA |
| Trityl chloride | $RNH_2$, $RCO_2H$, ROH, RSH | 1–5% TFA |
| 2-Methoxytrityl chloride | $RNH_2$, $RCO_2H$, ROH, RSH | 1–5% |
| Rink amide resin | $RCO_2H$ | 95% TFA |
| Sieber amide resin | $RCO_2H$ | 1% TFA |
| 4-Sulfamyl-benzoyl | $RCO_2H$ | Alkylation/amines |
| Wang resin | ROH, ArOH, $RNH_2$, $RCO_2H$ | 15–95% TFA or DDQ or CAN |
| HMPB-BHA | ROH, ArOH, $RCO_2H$ | 1% TFA |
| Bromoethyl photolinker | $RNH_2$, $RCO_2H$, ROH, RSH | hv |
| Hydroxy ethyl photolinker | $RCO_2H$ | hv |
| Aminoethyl photolinker | $RCO_2H$ | hv |

Structures

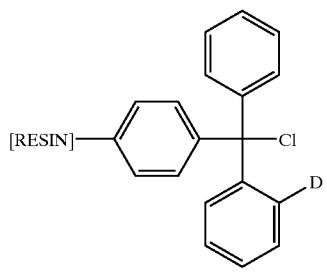

D = Cl: 2-chlorotrityl chloride type
D = H: trityl chloride type
D = OMe: 2-methoxytrityl chloride

Rink amide type

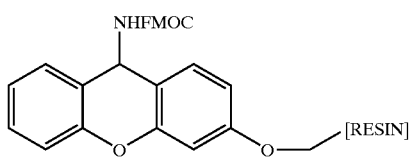

Sieber amide type

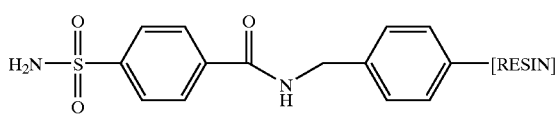

4-sulfamyl-benzoyl type

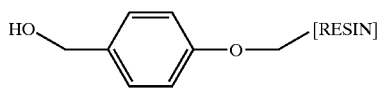

Wang type

| Structures | |
|---|---|
| 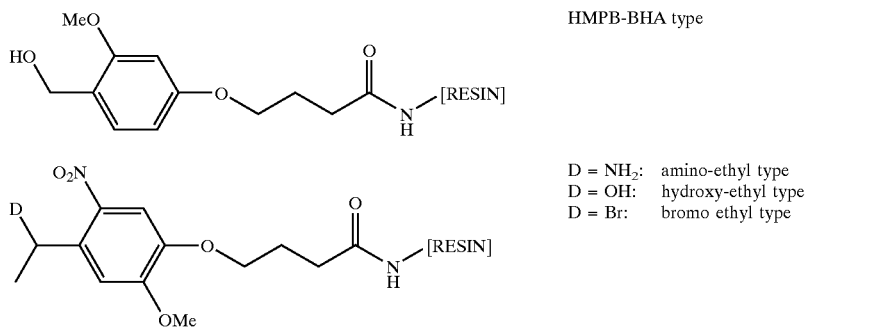 | HMPB-BHA type |
| | D = NH₂: amino-ethyl type<br>D = OH: hydroxy-ethyl type<br>D = Br: bromo ethyl type |

For CPI precursors the most preferred linking group is one which may be deemed photolytically cleavable. Further, the Rink amide linker is particularly suitable.

It is also possible that the linking group is a simple functionality provided on the solid support, e.g. amine, and in this case the linking group may be not be readily cleavable. This type of linking group is useful in the synthesis of large split and mix libraries which will be subjected to on-bead screening (see below), where cleavage is unnecessary. Such resins are commercially available from a large number of companies including NovaBiochem, Advanced ChemTech and Rapp Polymere. These resins include amino-Tentagel and aminomethylated polystyrene resin.

Combinatorial Unit

The term 'combinatorial unit' means any monomer unit which can be used to build a chain attached to the solid support, usually by a linking group. Usually combinatorial units will comprise at least two different functional groups to provide them with this chain building ability. For example, amino acids comprise both carboxylic acid and amine moieties. Sometimes the combinatorial unit may require more than two functionalities, e.g. if it has to bond to a further moiety. Examples of molecules suitable for such chain building are found in Schreiber et al. (JACS, 120. 1998, pp.23–29), which is incorporated herein by reference. An important example of a unit is an amino acid residue. Chains may be synthesised by means of amine-protected amino acids. Fmoc protected amino-acids are available from a number of sources, such as Sigma and Nova Biochem. Both natural and unnatural amino acids can be used, e.g. D- and L-amino acids and heterocyclic amino acids. In particular, heterocyclic amino acids of the type found in the construction of netropsin and distamycin are of interest because of their DNA-recognition properties.

Amine units can be used to make up peptoids: see Soth, M. J. and Nowick, J. S. 1997, Unnatural oligomer libraries, Curr. Opin, Chem. Biol. 1, no. 1: 120–129; Zuckermann et al., 1994, Discovery of Nanomolecular Ligands for 7-Transmembrane G-Protein-Coupled Receptors from a Diverse N-(Substituted) glycine Peptoid Library, Journal of Medicinal Chemistry 37: 2678–85; Figliozzi, GMR et al., 1996, Synthesis of N-substituted Glycine Peptoid Libraries, Methods in Enzymology, 267: 437–47; Simon, R J et al., 1992, Peptoids: A Modular Approach to Drug Discovery, Proc. Natl. Acad. Sci. USA, 89:9367–71; which are all incorporated herein by reference.

Other combinatorial units include PNAs (peptidonucleic acids): P E Nielsen, et al, Science, 1991, 254, 1497; M Egholm, et al, Nature, 1993, 365, 566; M Egholm et al, JACS, 1992, 114, 1895; S C Brown, et al, Science, 1994, 265, 777; 5. K Saha, et al, JOC, 1993, 58, 7827; oligoureas: Burgess K, et al, 1995, Solid Phase Synthesis of Unnatural Biopolymers Containing Repeating Urea Units. Agnew. Chem. Int. Ed. Engl 34, no. 8:907; Burgess K, et al, 1997, Solid Phase Synthesis of Oligoureas; Journal of the American Chemical Society 119: 1556–64; and oligocarbamates: Moran E J et al, 1995, Novel Biopolymers for Drug Discovery. Biopolymers (Peptide Science); John Wiley and Sons 37: 213–19; Cho C Y et al, 1993, An Unnatural Biopolymer. Science 261: 1303–5; Paikoff S F et al, 1996, The Solid Phase Synthesis of N-Alkylcarbamate Oligomers. Tetrahedron Letters 37, no. 32: 5653–56. All of these documents are incorporated herein by reference.

A further aspect of the present invention relates to combinatorial units having formula I, where the fused ring collectively represented by A and B is substituted by $CO_2R$.

Further combinatorial units of relevance to this invention are those of formulae (XIa/b):

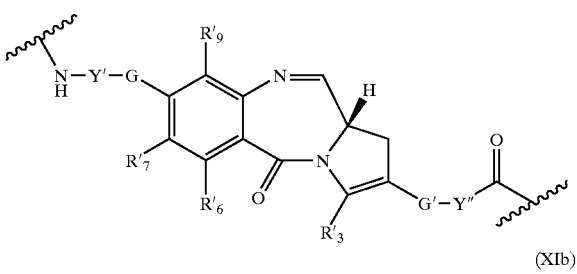
(XIa)

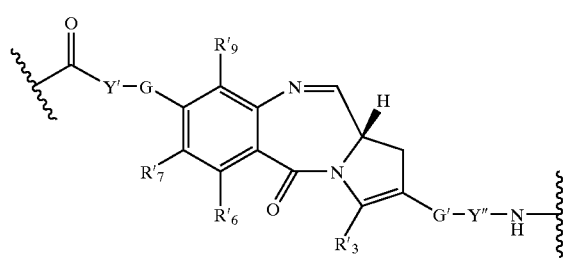
(XIb)

wherein $R'_3$, $R'_6$, $R'_7$, $R'_{19}$, G and Y' are as defined in the twelfth aspect of the invention, and G' and Y" are independently selected from the possible groups for G and Y' respectively. In order to synthesise combinatorial chains containing such combinatorial units, the units may need to be joined to the chain in their protected form (see definition of groups D(b) above). It is possible that the combinatorial units may remain in their protected form until the compound is cleaved from the solid support, or until the other components in the compound are deprotected.

Combinatorial units may also be of formula I with substituents as defined in the second aspect of the invention, where the fused ring, represented by -A-B-, bears a substituent which is —$CO_2H$ or —$CO_2R$.

The present invention relates to libraries, or collections, of compounds, all of which are represented by a single one of the formulae II, II', III, III', IV, IV', V, V', VII, VIII, 1× or X. The diversity of the compounds in a library may reflect the presence of compounds differing in the identities of one or more of (as appropriate) X, Y, Y', A, B, $R_2$, $R_7$, X', Y", G, $R'_2$, $R'_3$, $R_6$, $R'_7$, $R_{19}$, $R_{10}$, Q', $R_{111}$ and/or in the identities of the combinatorial units T, T', T" and T'" (when present). The number of members in the library depends on the number of variants, and the number of possibilities for each variant. For example, if it is the combinatorial units which are varied, and there are 3 combinatorial units, with 3 possibilities for each unit, the library will have 27 compounds. 4 combinatorial units and 5 possibilities for each unit gives a library of 625 compounds. If, for instance, there is a chain of 5 combinatorial units with 17 possibilities for each unit, the total number of members in the library would be 1.4 million. A library may therefore comprise more than 1 000, 5 000, 10 000, 100 000 or a million compounds, which may be arranged as described below.

In the case of free compounds (formulae II, II', IV, IV', VIII, X) the individual compounds are preferably in discrete volumes of solvents, e.g. in tubes or wells. In the case of bound compounds (formulae III, III', V, V', VII, IX) the individual compounds are preferably bound at discrete locations, e.g. on respective pins/crowns or beads. The library of compounds may be provided on a plate which is of a suitable size for the library, or may be on a number of plates of a standard size, e.g. 96 well plates. If the number of members of the library is large, it is preferable that each well on a plate contains a number of related compounds from the library, e.g. from 10 to 100. One possibility for this type of grouping of compounds is where only a subset of the combinatorial units, or substituents, are known and the remainder are randomised; this arrangement is useful in iterative screening processes (see below). The library may be presented in other forms that are well-known.

A further aspect of the present invention is a method of preparing a diverse collection, or library of compounds, as discussed above. If the diversity of the library is in the combinatorial units, then the library may be synthesised by the stepwise addition of protected combinatorial units to a CPI/CBI precursor core, each step being interposed by a deprotection step. Such a method is exemplified later. Libraries of this type can be prepared by the method known as "split and mix" which is described in Furka, A; Sebestyen, F; Asgedom, M and Dibo, G; General Method of Rapid Synthesis of Multicomponent Peptide Mixtures; International Journal of Peptide and Protein Research; 1991, 37, 487–193, which is incorporated herein by reference. If the diversity of the library is in the substituent groups, the library may be synthesised by carrying out the same synthetic methods on a variety of starting materials or key intermediates, which already possess the necessary substituent patterns.

The present invention also relates to a method of screening the compounds of formula II, II', III, III', IV, IV', V, V', VII, VIII, IX or X to discover biologically active compounds. The screening can be used to assess the binding interaction with nucleic acids, e.g. DNA or RNA, or proteins, or to assess the affect of the compounds against protein—protein or nucleic acid-protein interactions, e.g. transcription factor DP-1 with E2F-1, or estrogen response element (ERE) with human estrogen receptor (a 66 kd protein which functions as a hormone-activated transcription factor, the sequence of which is published in the art and is generally available). The screening may also be used to assess the cytotoxicity of the compounds against a variety of cell lines. The screening can be carried out by bringing the target macromolecules into contact with individual compounds or the arrays or libraries of individual compounds described above, and selecting those compounds, or wells with mixtures of compounds, which show the strongest effect.

This effect may simply be the cytotoxicity of the compounds in question against cells or the binding of the compounds to nucleic acids. In the case of protein—protein or nucleic acid-protein interactions, the effect may be the disruption of the interaction studied.

The binding of the compounds to nucleic acids may be assessed by labelling oligomers which contain a target sequence, and measuring the amount of labelled oligomers that bind to the compounds tested. The labelling may either be radiolabelling, or alternatively be labels detectable under visible or ultra-violet light. If this latter form of screening is carried out on compounds bound to solid supports which are in separate locations, the screening for results can be carried out visually under a microscope. A similar technique is described in detail in DNA-Binding ligands from peptide libraries containing unnatural amino acids, Lescrinier et al., *Chem Eur J*, 1998, 425–433. These techniques are particularly suited to a one-step screening of a complete library of compounds, especially a large library made by the "split and mix" method described above.

Protein-protein interactions can be measured in a number of ways, e.g. FRET (fluorescence resonance energy transfer) which involves labelling one of the proteins with a fluorescent donor moiety and the other with an acceptor which is capable of absorbing the emission from the donor; the fluorescence signal of the donor will be altered depending on the interaction between the two proteins. Another method of measuring protein—protein interactions is by enzymatic labelling, using, for example, horseradish peroxidase.

The screening process may undergo several iterations by selecting the most active compounds, or group of compounds, tested in each iteration; this is particular useful when testing arrays of wells which include mixtures of related compounds. Furthermore, if the wells contain compounds for which only a subset of the combinatorial units, or substituents, are known, but the rest are randomised, subsequent iterations can be carried out by synthesising compounds possessing the selected known (and successful) combinatorial unit, or substituent, pattern, but with further specified combinatorial units, or substituents, replacing the previously randomised combinatorial units, or substituents, adjacent the already known pattern; the remaining combinatorial units, or substituents, are randomised as in the previous iteration. This iterative method enables the identification of active members of large libraries without the need to isolate every member of the library.

A further feature of this aspect is formulation of selected compound or compounds with pharmaceutically acceptable carriers or diluents.

In yet further aspects, the invention provides a pharmaceutical composition comprising a compound of formula II, II', IV, IV', VIII or X and a pharmaceutically acceptable carrier or diluent; and the use of a compound of formula II, II', IV, IV', VIII or X in the manufacture of a medicament for the treatment of a gene-based disease, or a bacterial, parasitic or viral infection. Gene-based disease include neoplastic disease and, for example, Alzheimer's disease.

Compounds of formula II, II', IV, IV', VIII or X may be used in a method of therapy against a gene-based disease, such as cancer or Alzheimer's disease, or a viral, parasitic or bacterial infection.

Another aspect of the present invention relates to the use of compounds of formula III, III', V, V', VII or IX in diagnostic methods. A compound of formula III, III', V, V', VII or IX which binds to an identified sequence of DNA or a protein known to be an indicator of a medical condition can be used in a method of diagnosis. The method may involve passing a sample, e.g. of appropriately treated blood or tissue extract, over an immobilised compound of formula III, III', V, V', VII or IX, for example in a column, and subsequently determining whether any binding of target DNA to the compound of formula III, III', V, V', VII or IX has taken place. Such a determination could be carried out by passing a known amount of labelled target DNA known to bind to compound III, III', V, V', VII or IX through the column, and calculating the amount of compound III, III', V, V', VII or IX that has remained unbound.

A further aspect of the present invention relates to the use of compounds of formula II, II', IV, IV', VIII or X in target validation. Target validation is the disruption of an identified DNA sequence to ascertain the function of the sequence, and a compound of formula II, II', IV, IV', VIII or X can be used to selectively bind an identified sequence, and thus disrupt its function.

Another aspect of the present invention relates to the use of compounds of formulae II, II', IV, IV', VIII or X in functional genomics to ascertain the biological function of genes, by blocking this biological action.

Preferred Synthetic Strategies

Compounds of formula I can be synthesised by applying the methods described below. A review of methods of synthesising CPIs was carried out by Boger (Boger, D. L. et al., J. A. *Chem. Rev.* 1997, 97, 787–828)

Boger Synthesis of N—BOC—CBI

Selective C4 iodination of N—BOC-4-(benzyloxy) naphthylamine, readily accessible in three steps from the commercially available 1,3-dihydroxynaphthalene, followed by N-alkylation with allyl bromide provided the required substrate for the 5-exo-trig aryl radical-alkene cyclization (Boger, D. L. et al., O. *J. Am. Chem. Soc.* 1989, 111, 6461–6463. Boger, D. L. at al., O. *J. Org. Chem.* 1990, 55, 5823–5832) (Scheme 1). Treatment with Bu$_3$SnH-TEMPO (Boger, D. L.; McKie, J. A. *J. Org. Chem.* 1995, 3, 1429–1953) and subsequent reduction with Zn afforded the 3-(hydroxymethyl)indoline CBI precursor. Conversion to the primary chloride and catalytic hydrogenolysis of the benzyl ether, followed by direct resolution on a semipreparative chiral HPLC column afforded both enantiomers (Boger, D. L.; Yun, W. *J. Am. Chem. Soc.* 1994, 116, 7996–8006). Subsequent spirocyclization completed the synthesis.

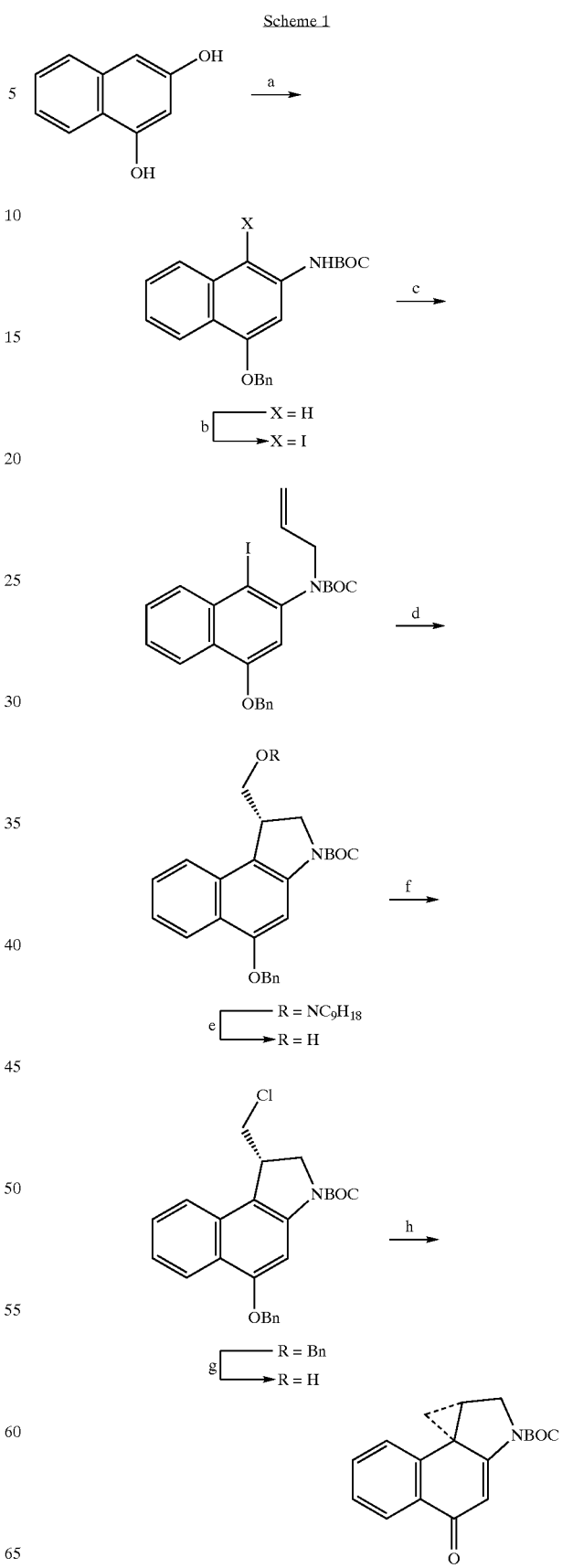

Reagents and conditions: a: NH$_3$, BOC$_2$O; BnBr; b: NIS; c: AllylBr, NaH; d: BU$_3$SnH, TEMPO; e: Zn; f: Ph$_3$P—CCl$_4$; g: H$_2$, Pd—C; h: NaH Cava Synthesis of CBI Cava's route to CBI uses a heterocyclization procedure involving a heterostilbene to establish the tricyclic CBI core, followed by introduction of an additional functionalized carbon necessary for formation of the cyclopropane (Drost, K. J.; Cava, M. P. *J. Org. Chem.* 1991, 56, 2240–2244) (Scheme 2).

Scheme 2

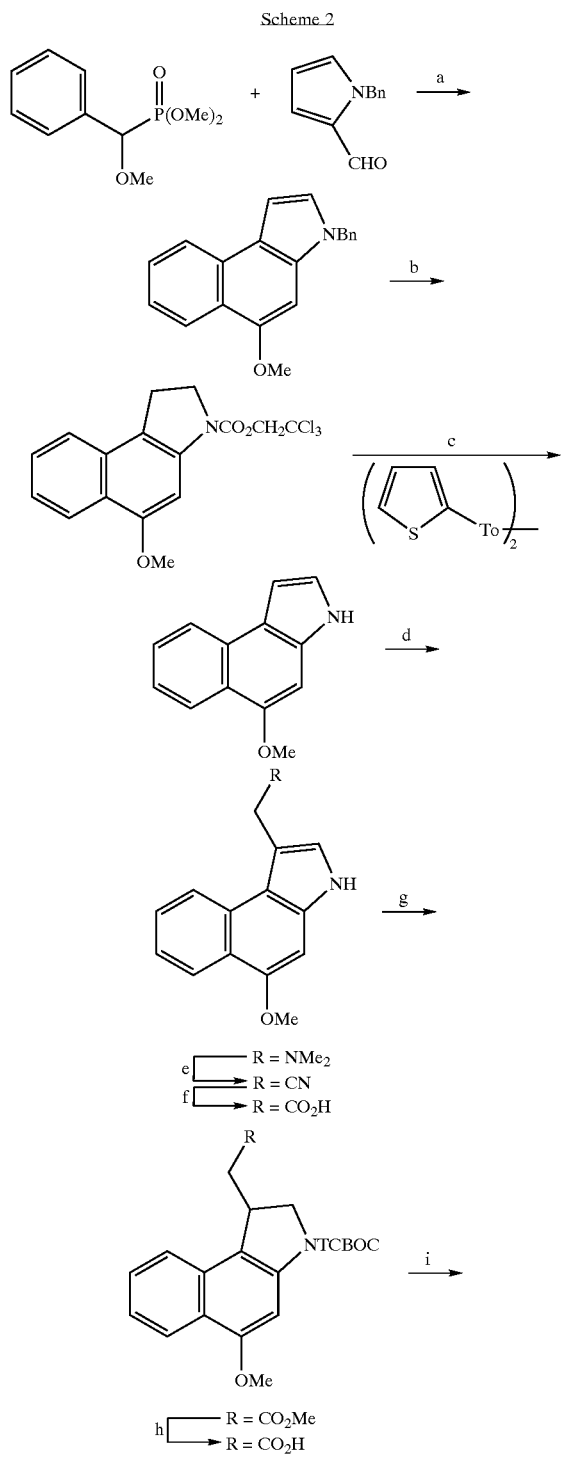

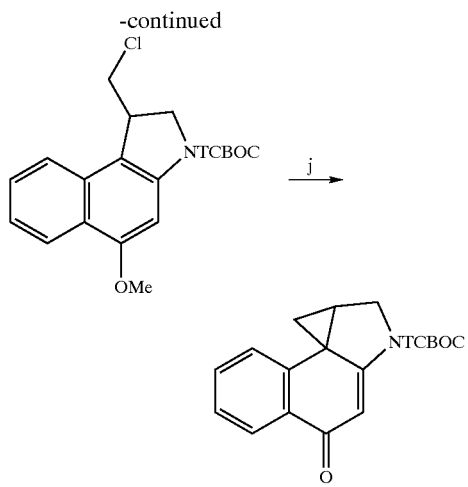

Reagents and conditions: a: 1) t-BuOK; 2) p-nitrobenzoic acid, Et$_3$N, Pd—C, hn; b: 1) NaBH$_3$CN; 2) ClCO$_2$CH$_2$CCl$_3$; C: 1) DDQ; 2) NaBH$_4$; d: Me$_2$NH, CH$_2$O; e: CH$_3$I; NaCN; f: NaOH; g: 1) MeO$_2$CCl, Et$_3$N; 2) NaBH$_3$CN; 3) TCBOC-CL, Et$_3$N; h: NaOH; i: 1) (COCl)$_2$; 2) mercaptopyridine-N-oxide, DMAP, CCl$_4$; j: BCl$_3$—SMe$_2$; Et$_3$N Thus, photolysis of the alkene formed from condensation of the α-methoxybenzyl phosphonate with N-benzylpyrrole-2-carboxaldehyde in the presence of Pd—C provided the tricylic CBI core (Rawal, V. H.; Jones, R. J.; Cava, M. P. *J. Org. Chem.* 1987, 52, 19–28). A four step debenzylation sequence followed by a regioselective Mannich alkylation was employed to provide the key CBI intermediate.

Aristoff Synthesis of CBI (Scheme 3)

An alternative approach to the CBI subunit was described by Aristoff and coworkers (Aristoff, P. A.; Johnson, P. D.; Sun, D. *J. Med. Chem.* 1993, 36, 1956–1963. Aristoff, P. A.; Johnson, P. D. *J. Org. Chem.* 1992, 57, 6234–6239). 1-Allyl-2-(benzylamino)-1-hydroxydihydronaphthalenone was prepared in two steps from 1,4-naphthoquinone. Reduction and re-aromatization was accomplished by treatment with BOC$_{20}$ followed by sodium dithionite. The racemic diol was prepared by OsO$_4$-catalyzed dihydroxylation. Deprotection of the benzylamine, N— and O-acetylation, acetate hydrolysis, followed by selective mesylation of the primary alcohol and TMS ether protection of the secondary alcohol preceded 6-membered ring closure upon treatment with NaH. Alcohol deprotection and resolution by chromatographic separation of the diastereomeric (R)—O-acetylmandelate esters provided the optically active materials.

Scheme 3

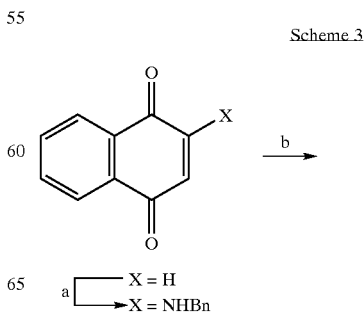

-continued

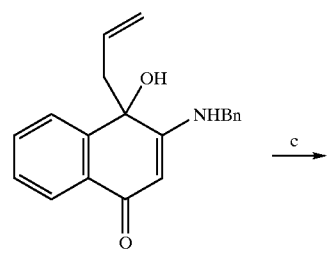

c →

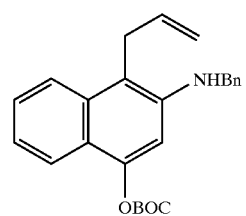

d →

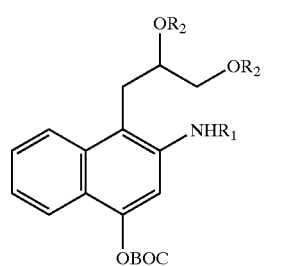

e ⌐ R₁ = Bn, R₂ = H
  └→ R₁ = Ac, R₂ = Ac
f ⌐
  └→ R₁ = Ac, R₂ = H g →

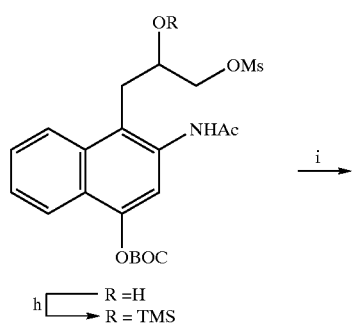

h ⌐ R = H
  └→ R = TMS i →

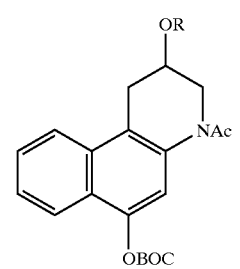

k →

-continued

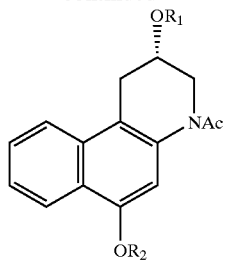

i ⌐ R₁ = H, R₂ = BOC
  └→ R₁ = Ms, R₂ = BOC
l ⌐
  └→ R₁ = Ms, R₂ = H m →

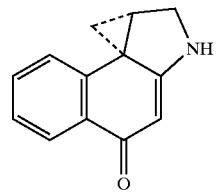

Reagents and conditions: a: BnNH₂; b; Allyl MgBr; c: BOC₂O; Na₂S₂O₄; d: OsO₄, NMO; e: HCO₂H, Pd—C; Ac₂O; f: K₂CO₃; g: TMSCl, pyridine; h: NaH; j: K₂CO₃; k: (R)—O-acetylmandelic acid, EDCI; Resolution; K₂CO₃; i: MsCl, Et₃N; l: TFA; m: NaH Primary alcohol activation, BOC deprotection, and transannular cyclization upon treatment with NaH provided the CBI accompanying hydrolysis of the intermediate N—Ac—CBI by water present in the reaction mixture.

Any of these three routes may be adapted to synthesise compounds according to the first aspect of the present invention, for example by starting with appropriately substituted starting materials (which may be protected), or by introducing substituents at a later stage.

Preferred Synthetic Strategies of pyrrolo[2,1-c][1,4] benzodiazepines (also see WO 00/12506)

A key step in a preferred route to compounds corresponding to the group D(b) of the eleventh aspect of the invention or combinatorial units of formulae XIa and XIb is a cyclisation process to produce the B-ring, involving generation of an aldehyde (or functional equivalent thereof) at what will be the 11-position, and attack thereon by the pro-10-nitrogen:

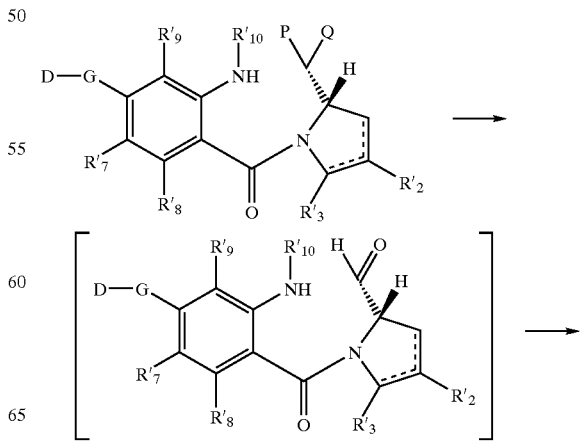

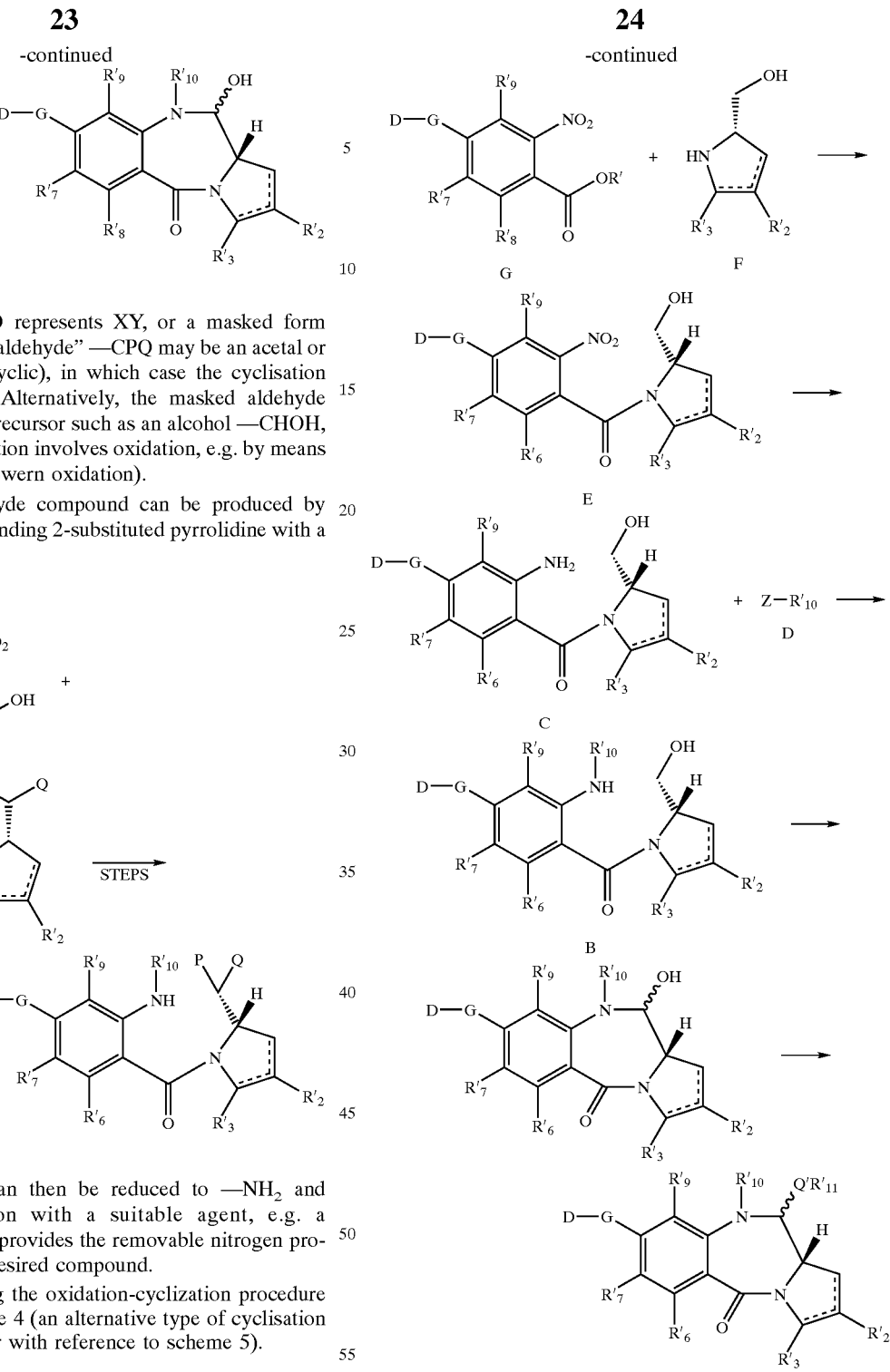

In this structure, D represents XY, or a masked form thereof. The "masked aldehyde" —CPQ may be an acetal or thioacetal (possibly cyclic), in which case the cyclisation involves unmasking. Alternatively, the masked aldehyde may be an aldehyde precursor such as an alcohol —CHOH, in which case the reaction involves oxidation, e.g. by means of TPAP or DMSO (Swern oxidation).

The masked aldehyde compound can be produced by condensing a corresponding 2-substituted pyrrolidine with a 2-nitrobenzoic acid:

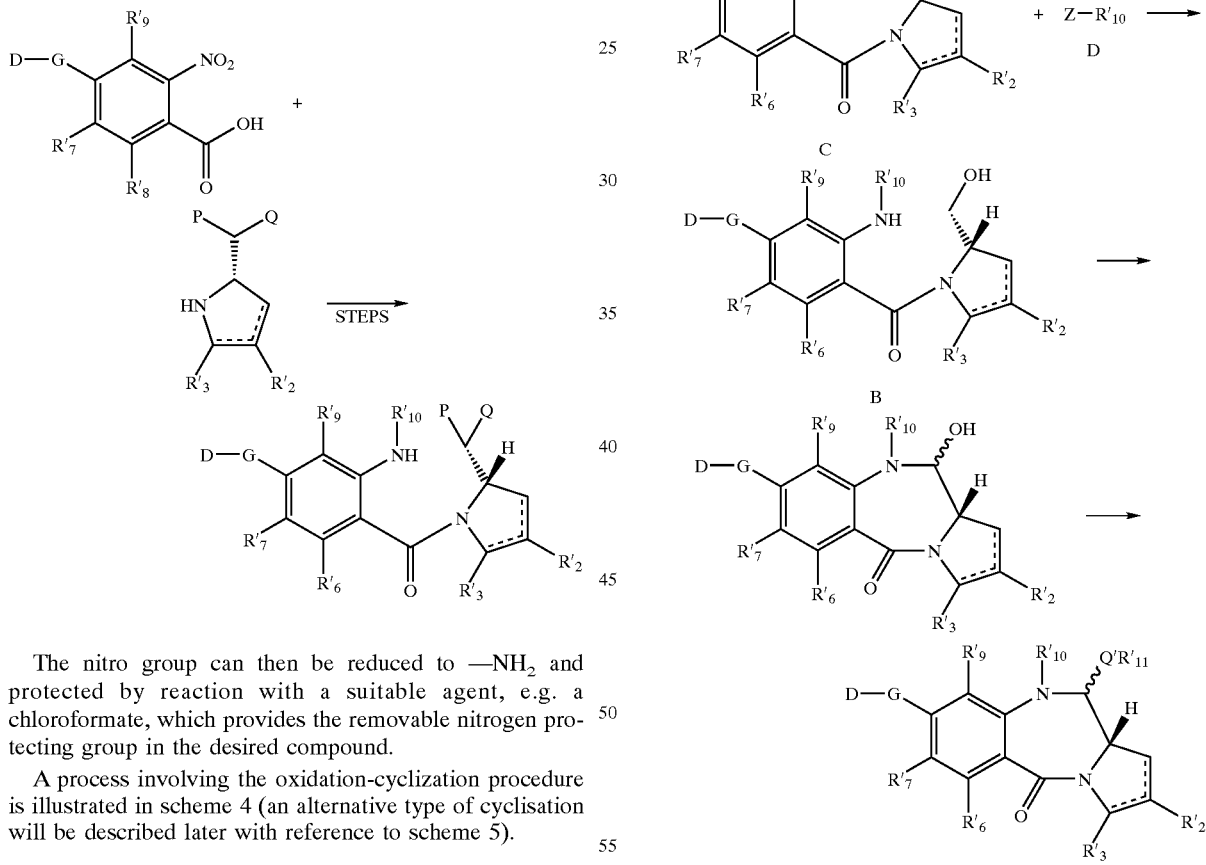

The nitro group can then be reduced to —NH$_2$ and protected by reaction with a suitable agent, e.g. a chloroformate, which provides the removable nitrogen protecting group in the desired compound.

A process involving the oxidation-cyclization procedure is illustrated in scheme 4 (an alternative type of cyclisation will be described later with reference to scheme 5).

Scheme 4

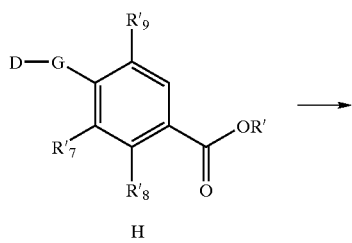

If R'$_{11}$ is other than hydrogen, the final compound may be prepared by direct etherification of the alcohol. Compounds with Q'=S can be prepared by treatment of the corresponding alcohol with R'$_{11}$SH, and a catalyst (usually a Lewis Acid such as Al$_2$O$_3$). If Q'=NH, then these compounds can be prepared by reacting the alcohol with an amine R'$_{11}$NH and a catalyst (usually a Lewis Acid).

Exposure of the alcohol B (in which the 10-nitrogen is generally protected as an amide carbamate) to tetrapropylammonium perruthenate (TPAP)/N-methylmorpholine N-oxide (NMO) over A4 sieves results in oxidation accompanied by spontaneous B-ring closure to afford the desired product. The TPAP/NMO oxidation procedure is found to be particularly convenient for small scale reactions while the use of DMSO-based oxidation methods, particularly Swern oxidation, proves superior for larger scale work (e.g. >1 g).

The uncyclized alcohol B may be prepared by the addition of a nitrogen protecting reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable.

The nitro compound of formula E may be prepared by coupling the appropriate o-nitrobenzoyl chloride to a compound of formula F, e.g. in the presence of $K_2CO$, at −25° C. under a $N_2$ atmosphere. Compounds of formula F can be readily prepared, for example by olefination of the ketone derived from L-trans-4-hydroxy proline. The ketone intermediate can also be exploited by conversion to the enol triflate for use in palladium mediated coupling reactions.

The o-nitrobenzoyl chloride is synthesised from the o-nitrobenzoic acid (or alkyl ester after hydrolysis) of formula G, which itself is prepared from the vanillic acid (or alkyl ester) derivative H. Many of these are commercially available and some are disclosed in Althuis, T. H. and Hess, H. J., *J. Medicinal Chem*, 20(1), 146–266 (1977).

Alternative Cyclisation (Scheme 5)

Scheme 5

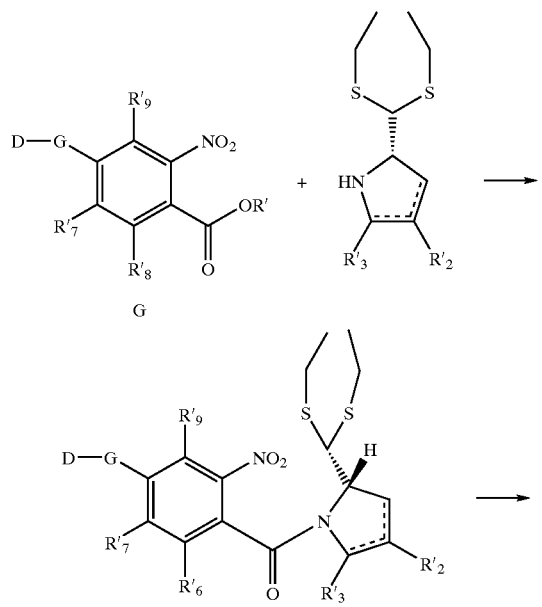

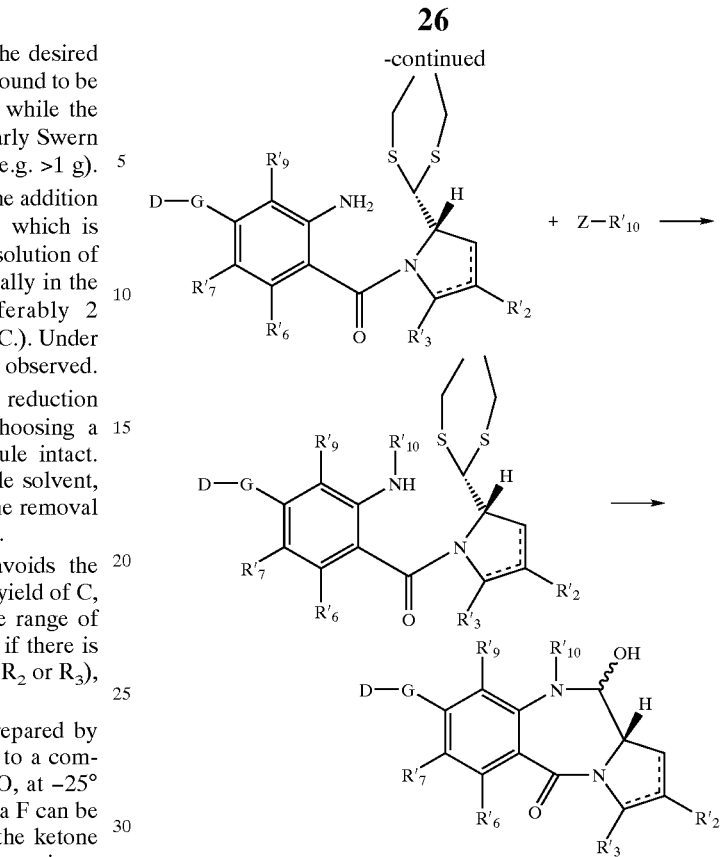

In scheme 4, the final or penultimate step was an oxidative cyclisation. An alternative approach, using thioacetal coupling/unmasking, is shown in scheme 5. Mercury-mediated unmasking causes cyclisation to the desired compound.

The thioacetal intermediates may be prepared as shown in scheme 2: the thioacetal protected C-ring [prepared via a literature method: Langley, D. R. & Thurston, D. E., *J. Organic Chemistry*, 52, 91–97 (1987)] is coupled to the o-nitrobenzoic acid (or alkyl ester after hydrolysis) G using a literature procedure. The resulting nitro compound cannot be reduced by hydrogenation, because of the thioacetal group, so the tin(II) chloride method is used to afford the amine. This is then N-protected, e.g., by reaction with a chloroformate or acid chloride, such as p-nitrobenzylchloroformate.

Acetal-containing C-rings can be used as an alternative in this type of route with deprotection involving other methods including the use of acidic, or perhaps Lewis Acid, conditions.

In the above synthesis schemes, the derivatisation of the A-ring is shown as being complete before the compounds are attached to the solid support. This is preferred is the substituents are groups such as alkoxy or nitro. On the other hand, substituent groups such as alkyl or alkenyl could be added to the A-ring after the coupling of the compound to the solid support. This may be achieved by $R'_6$, $R'_7$, or $R'_9$ being easily replaceable groups, such as a halogen atom.

An alternative synthesis approach to those detailed above is to protect the Pro N10 position on the component which will form the A-ring before joining the component which will form the C-ring.

Embodiments of the present invention will now be described by way of example.

EXAMPLE 1

CBI Bound to TG-Carboxy Resin
Activation of TG-Carboxy resin with 3-hydroxy-1,2,3-benzotriazin-4(3H)-one (HO-Dhbt)

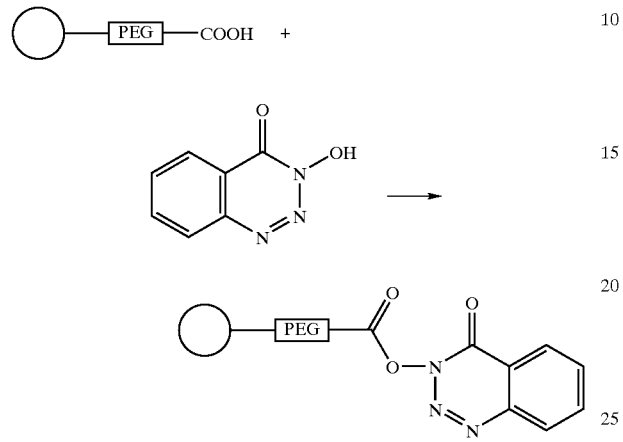

TG Carboxy resin (Nova-Biochem, 80 mg 0.020 mmol) was suspended and swollen in DMF (1 mL) for 10 minutes. DMF was removed by suction and the resin treated with diisopropyl carbodiimide (DIC) (34 mmL, 10 eq) in of DMF (1 mL). The mixture was shaken for 15 minutes at −15° C. (acetone-ice bath), then rinsed with DMF (2×1 mL).

The resin was suspended in DMF(1 mL), cooled to −10° C. and treated with HO-Dhbt(33 mg, 10 eq). The mixture was shaken for 30 minutes at −10° C., followed by 4 hours shaking at 0° C. and was then allowed to stand at 0° C. overnight.

The reaction mixture was filtered and the resin washed with DMF (2×1 mL), dichloromethane (2×1 mL), MeOH (2×1 mL) and diethyl ether (1 mL). The activated resin was stored in freezer until ready for use.

Coupling of O-Dhbt Activated TG-Carboxy Resin with seco-CBI, in Presence of DIPEA Seco-CBI has a very limited storage time, and for this reason BOC-seco-CBI is deprotected immediately before coupling to the activated resin. BOC-seco-CBI (20 mg 0.06 mmol) was dissolved in HCl in anhydrous ethyl acetate (3M, 2.8 mL). The mixture was kept at 0° C. for 30 minutes and then allowed to warm to room temperature over 30 minutes. TLC (4:1 petroleum ether:diethyl ether) revealed complete reaction; the reaction mixture was evaporated under reduced pressure and stored at −20° C.

O-Dhbt activated resin (40 mg) was treated with seco-CBI dissolved in DMF (1 mL). DIPEA (3 eq, 7.7 mg, 10 mL) was added to the suspension and the mixture was shaken for 30 minutes at room temperature. The reaction mixture was filtered and the resin was washed with DMF (1 mL), dichloromethane (1 mL), methanol (1 mL) and diethyl ether (2×1 mL). After thorough evaporation of solvents the resin was stored at −20° C.

EXAMPLE 2 seco-CBI Bound to TG-Carboxy Resin

Coupling of O-Dhbt Activated TG-Carboxy Resin with eco-CBI, in Absence of Base

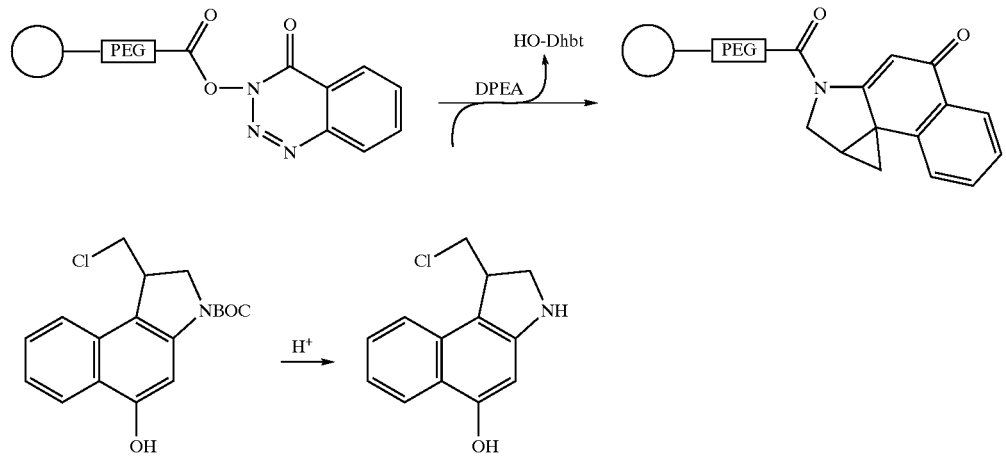

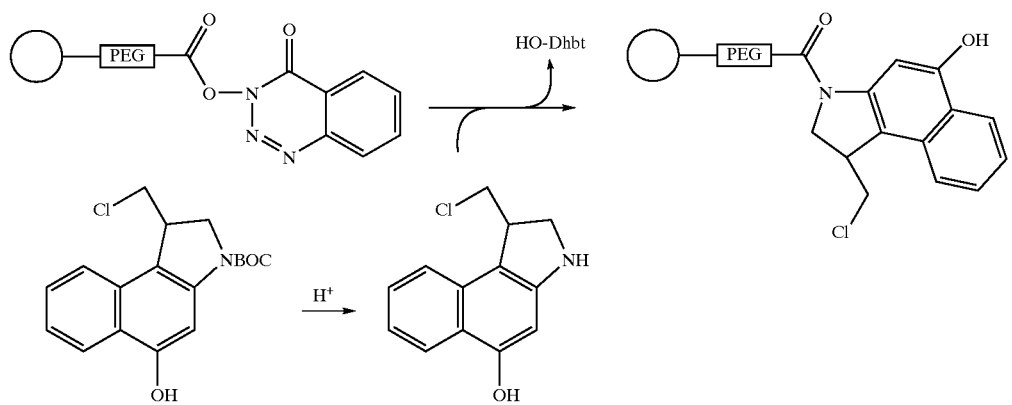

BOC-seco-CBI (20 mg, 0.06 mmol) was dissolved in HCl solution in anhydrous ethyl acetate (3M, 2.8 mL). The mixture was kept at 0° C. for 30 minutes and then allowed to warm to room temperature over 30 minutes. TLC (4:1= petroleum ether:diethyl ether) revealed complete reaction; the reaction mixture was evaporated at reduced pressure and directly used for the coupling without further purification.

O-Dhbt-activated resin (see Example 1) (40 mg, 0.01 mmol) was treated with seco-CBI dissolved in DMF (1 mL); the mixture was agitated for 1 hour at room temperature. The reaction mixture was then filtered and the resin was washed with DMF (1 mL), dichloromethane (1 mL), methanol (1 mL) and diethyl ether (2×1 mL). After thorough evaporation of excess solvent the resin was stored at −20° C.

EXAMPLE 3

Synthesis of a CBI—Hexapeptide Library
General Procedures
General Procedure for Acetylation/Endcapping After each coupling step the resin was treated with a mixture of pyridine (30%) and acetic anhydride (20%) in dichloromethane, to acetylate any free amino groups that had not been coupled to an amino acid. In this way the formation of undesirable oligopeptides (carrying less than the expected number of amino acids) could be avoided. The resin was treated with the acetylating reagent (3 mL) and the slurry was agitated at room temperature for 1 hour. The reagents were then removed by filtration and the resin was rinsed with dichloromethane (2×5 mL) and methanol (2×5 mL).

General Procedure for Fmoc Deprotection

The resin was treated with a solution of piperidine in DMF (20%, 3 mL). The mixture was then agitated for 2 hours at room temperature. Excess solvent was then removed by suction and the resin was rinsed with DMF (2×5 mL), dichloromethane (2×5 mL) and methanol (2×5 mL).

Library Generation
Fmoc-Glu-OAll Coupled to NovaSyn TG Resin

NovaSyn TG amino resin (0.345 g, load 0.29 mmol/g, 0.1 mmol) was suspended and swollen in DMF (2 mL), under agitation (1000 rpm) for 30 minutes. Excess solvent was then removed and a solution of Fmoc-Glu-OAll (0.123 g, 0.3 mmol, 3 eq), TBTU (0.096 g, 0.3 mmol, 3 eq) and DIPEA (0.052 mL, 0.3 mmol, 3 eq) in DMF (3 mL) was added to the swollen resin. The resulting mixture was agitated at 1000 rpm at room temperature, overnight. The reaction mixture was filtered and the resin rinsed with DMF (2×2 mL), dichloromethane (2×5 mL) and methanol (2×5 mL).

The resin was then acetylated (see General procedure for acetylation) and deprotected (see General procedure for Fmoc deprotection).

HO-Gly-Fmoc coupled to P-Glu (OAll)-H

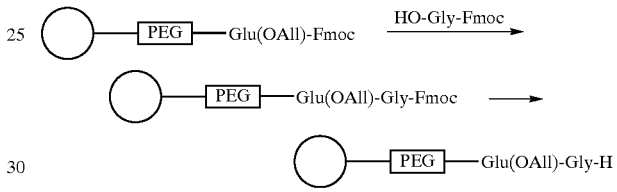

The resin was suspended in DMF (2 mL) and allowed to swell for 30 minutes at room temperature, accompanied by agitation (1000 rpm). Excess DMF was removed and a solution of Fmoc-Gly-OH (0.089 g, 0.3 mmol, 3 eq), TBTU (0.096 g, 0.3 mmol, 3 eq) and DIPEA (0.052 mL, 0.3 nmol, 3 eq) in DMF (3 mL) was added to the resin. The mixture was allowed to shake at room temperature for 12 hours. Excess reagents were then removed by filtration and the resin was rinsed with DMF (2×5 mL), dichloromethane (2×5 mL) and methanol (2×5 mL). The resin was then acetylated (see General procedure for acetylation) and deprotected (see General procedure for Fmoc deprotection) to afford the resin-bound dipeptide P-Glu (OAll)-Gly-H.

Split & Mix Procedure for the Resin Bound Hexapeptide P-Glu (OAll)-Gly-$X_1X_2X_3X_4$—H sublibrary

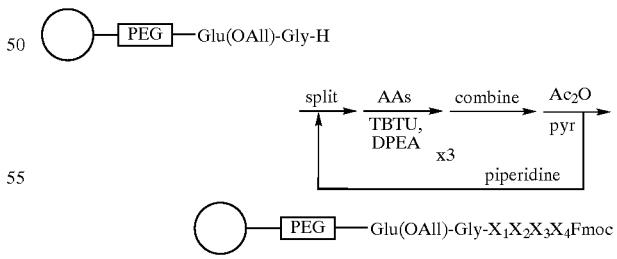

The resin was suspended in 3:1 mixture of 1,2-dichloroethane (DCE) and DMF and equally partitioned into 17 4 mL Alltech tubes. Each tube thus contained 0.1/17 mmol=5.88 $10^{-6}$ mol of resin-bound dipeptide. Excess solvent was removed in vacuo, and the resin was suspended in DMF (200 mL) and agitated for 30 minutes. The 17 amino acids (1.76 $10^{-5}$ mmol, 3 eq for each step, 7.04 $10^{-5}$ mmol for 4 steps) were weighed into 17 vials:

| | | |
|---|---|---|
| 1. Fmoc-Ala-OH | 22 mg |
| 2. Fmoc-Asn-OH | 25 mg |
| 3. Fmoc-Asp(OtBu)-OH | 29 mg |
| 4. Fmoc-Gln-OH | 26 mg |
| 5. Fmoc-Glu(OtBu)-OH | 30 mg |
| 6. Fmoc-Gly-OH | 21 mg |
| 7. Fmoc-Ile-OH | 25 mg |
| 8. Fmoc-Leu-OH | 25 mg |
| 9. Fmoc-Lys(BOC)-OH | 33 mg |
| 10. Fmoc-Met-OH | 26 mg |
| 11. Fmoc-Phe-OH | 27 mg |
| 12. Fmoc-Pro-OH | 24 mg |
| 13. Fmoc-Ser(tBu)-OH | 27 mg |
| 14. Fmoc-Thr(tBu)-OH | 28 mg |
| 15. Fmoc-Trp(BOC)-OH | 37 mg |
| 16. Fmoc-Tyr(tBu)-OH | 32 mg |
| 17. Fmoc-Val-OH | 24 mg |

Each amino acid was dissolved in DMF (2 mL); an aliquot of each solution (0.5 mL, corresponding to 1.76 $10^{-5}$ mmol, 3 eq of each amino acid) was added to the appropriate tube. TBTU (1.76 $10^{-5}$ mmol×17=2.99 $10^{-4}$, 96 mg) and DIPEA (1.76 $10^{-5}$ mmol×17=2.99 $10_{-4}$, 52 mL) were separately dissolved in DMF (1.7 mL) and each solution was evenly distributed, delivering 3 eq of each reagent, to each one of the 17 tubes.

The reaction tubes were agitated at room temperature for 12 hours, then the reagents and solvents were removed in vacuo and the resin was rinsed with DMF (2×1 mL each tube), DCM (2×1 mL each tube) and methanol (2×1 mL each tube). The resin was then suspended in 3:1 mixture of 1,2-dichloroethane and DMF and recombined. The recombined resin was acetylated (3 mL of acetylating reagent, 1 hour, room temperature) and deprotected (3 mL of 20% piperidine in DMF, 2 hours, room temperature).

The procedure was repeated 3 more times. At the end of the $4^{th}$ amino acid coupling the deprotection step was not executed.

Deprotection of Allyl Ester

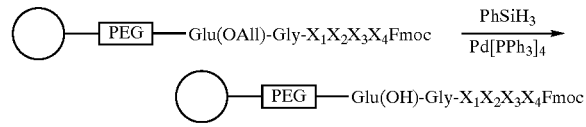

The resin was suspended in DCM (2 mL), phenylsilane (2.4 mmol, 24 eq, 0.29 mL) in DCM (1 mL) of was added and the mixture was shaken at room temperature for 10 minutes.

A catalytic amount of Pd[PPh$_3$]$_4$ (0.01 mmol, 0.1 eq, 11 mg) in DCM (0.5 mL) was added and the reaction mixture was shaken for further 10 minutes.

The reagents were filtered and the resin was rinsed with DCM (2×5 mL) and methanol (2×5 mL). The procedure was repeated once again and the resin was finally dried under reduced pressure.

Activation of Resin with 3-hydroxy-1,2,3-benzotriazin-4 (3H)-one (Ho-Dhbt)

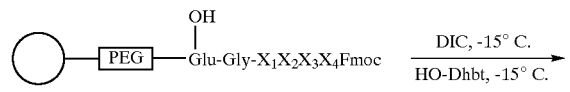

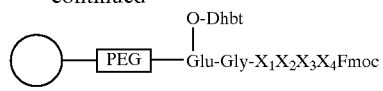

The resin was suspended and swollen in DMF (2 mL) for 10 minutes. Excess DMF was removed and the resin was treated with a solution of diisopropyl carbodiimide (DIC) (156 mL, 1 mmol, 10 eq) in DMF (2 mL). The resulting slurry was shaken for 15 minutes at −15° C. (acetone-ice bath), then washed with DMF (2×2 mL).

The resin was resuspended in DMF (2 mL), cooled to −10° C. and treated with HO-Dhbt (163 mg 1 mmol, 10 eq). The mixture was shaken for 30 minutes at −10° C., followed by 4 hours at 0° C. and then allowed to stand at 0° C. overnight.

The reaction mixture was filtered and the resin washed with DMF (2×2 mL), dichloromethane (2×2 mL), MeOH (2×2 mL) and diethyl ether (2 mL). The activated resin was stored in freezer until required for use.

Coupling of O-Dhbt Activated Resin with seco-CBI, in Presence of DIPEA

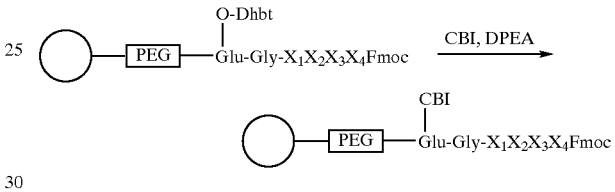

BOC-seco-CBI (see example 2) was deprotected immediately before coupling to the activated resin. BOC-seco-CBI (100 mg, 0.3 mmol) was dissolved in a solution of HCl in anhydrous ethyl acetate (3M, 15 mL). The mixture was cooled at 0° C. for 30 minutes and then allowed to warm to room temperature over 30 minutes. TLC (4:1=petroleum ether:diethyl ether) revealed complete reaction; the reaction mixture was evaporated under reduced pressure and stored at −20° C.

O-Dhbt-activated resin was treated with seco-CBI dissolved in DMF (2 mL) and the mixture was shaken for 60 minutes at room temperature. The reaction mixture was filtered and the resin was washed with DMF (2×2 mL), dichloromethane (2×2 mL), methanol (2×2 mL) and diethyl ether (2×1 mL). The resin was dried under reduced pressure and stored in a cool, dry place.

t-Butyl- and Boc- Deprotection on Side Chains

The resin was treated with a solution of TIS/TFA in dichloromethane (2%, 2 mL). The mixture was shaken for 2 hours at room temperature. Excess reagents were removed in vacuo and the resin was rinsed with dichloromethane (2×5 mL) and methanol (2×5 mL).

Fmoc Deprotection

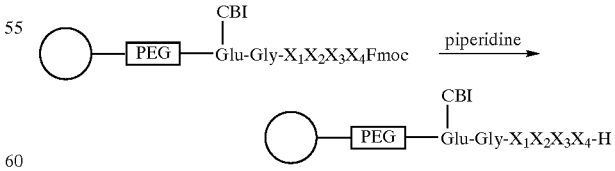

The resin was treated with a solution of piperidine in DMF (20%, 3 mL), and agitated at room temperature for 2 hours. The mixture was filtered and the resin was washed with DMF (2×5 mL), dichloromethane (2×5 mL) and m n ethanol (2×5 mL). The resin was then dried under reduced pressure.

Screening

The resulting library was screened against rhodamine labelled double strand ed DNA with the sequence Label-5'-GCG TAA AAA CGC=3'.

The sublibrary was mixed with the DNA sequence (5 pmol/mL) and incubated at 37° C. for 24 hours with occasional mixing. After 24 hours, the sublibrary was washed 4 times with TE buffer pH 7.6 or PBS. To identify the beads to which most labelled DNA had bound, agarose gel slides were prepared as follows. ~500 mL of 0.25% sea plaque agarose was layered onto a clean transparent slide and allowed to cool and set. The incubated beads were then mixed with another—500 mL of 0.25% sea plaque agarose solution and layered onto the precoated slides, and allowed to cool and set.

The reddest beads were identified by eye under a dissecting light microscope, and then retrieved by adding ~1 mL of water to dried agarose slide to enable their removal using a p10 gilson pipette with a fine tip. The removed beads were then placed into a 1 mL Eppendorf PCR tube ready for identification.

Identification

The identification of the sequences of the most active compounds was carried out using automated Edman degradation and reversed-phase HPLC.

Pulsed liquid-phase N-terminal sequencing was performed using an Applied Biosystems (ABI)477A automatic protein sequencer. The selected labelled beads were loaded onto a glass fibre disc which had previously been pre-cycled once. The disc was placed in the sequencer and pre-cycled once, then six cycles of Edman degradation were performed (Edman, P and Begg, G (1967) Eur. J. Biochem. 1, 80). The released phenylthiohydantion (PTH—) amino acid derivatives were identified by reversed-phase HPLC analysis.

The four most active compounds were those with the following sequences:

| | |
|---|---|
| CBI-QGVKKK | CBI-QGLVAG |
| CBI-QGNKKA | CBI-QGQKNS |

EXAMPLE 4

Synthesis of A CBI Combinatorial Building Block: 7-carboxy-1,2,9,9a-tetrahydrocyclopropa[c]benzo[e]indol-4-one The synthesis proceeds from a modified Stobbe condensation/Friedel-Crafts acylation for generation of the functionalised precursor, followed by 5-exo-trig aryl radical-alkene cyclization.

Wadsworth-Horner-Emmons condensation of 3-bromobenzaldehyde with the Sargent phosphonate predominantly provides the E-isomer, which in turn undergoes acid-catalyzed deprotection and Friedel-Crafts acylation (Scheme 6).

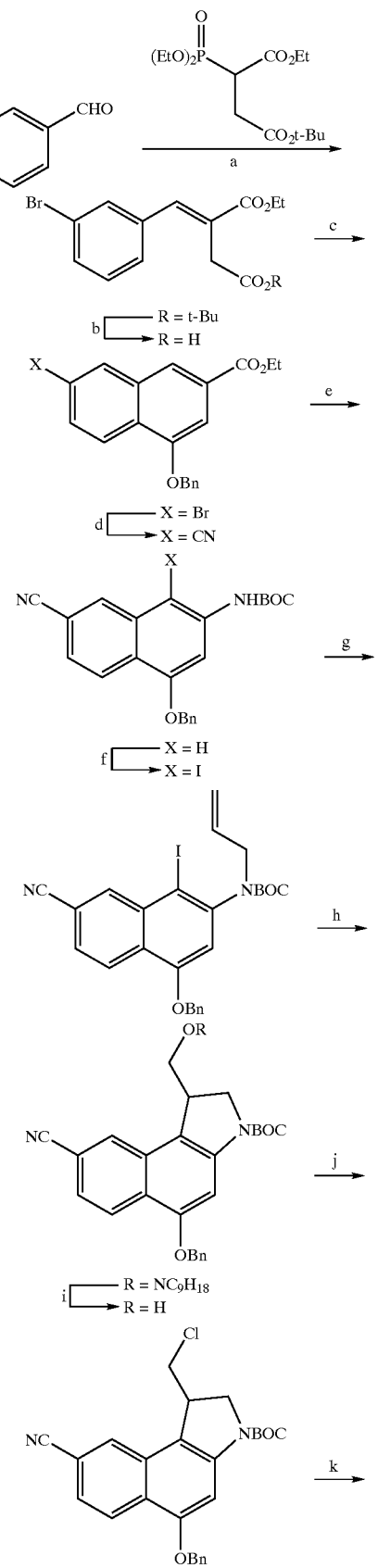

Scheme 6

-continued

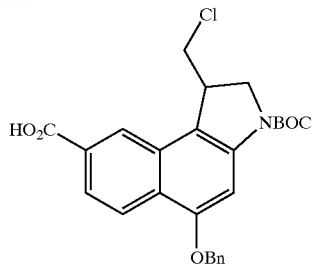

Reagents and conditions: a: NaH, Sargent phosphonate; b: TFA;
c: 1) Ac₂O—KOAc; 2) K₂CO₃; 3) BnBr, K₂CO₃; d: CuCN; e: 1) LiOH;
2) DPPA, t-BuOH; f: NIS; g: allyl Br, NaH; h: Bu₃SnH, TEMPO;
i: Zn—HOAc; j: Ph₃P—CCl₄; k: NaOH Aromatic nucleophilic substitution, ester hydrolysis and Curtius rearrangement effected by treatment with DPPA are followed by regioselective C4 iodination and N-alkylation with allyl bromide. The aryl radical-alkene cyclization by means of TEMPO as radical trap, as described in Boger synthesis of CBI, provides the tricyclic system that, after conversion to the primary chloride and base-catalyzed hydrolysis of the cyano group, should give the desired building block for a combinatorial library.

EXAMPLE 5

Screening of CBI on Bead Against DNA Sequence

The CBI on bead synthesised in example 1 was screened against rhodamine labelled double stranded DNA with the sequence: Label-5'-GCG TAA AAA CGC-3'.

For comparison, indoline was added to O-Dhbt-activated TG Carboxy resin (as prepared in example 1) to yield a comparative resin that does not covalently interact with DNA.

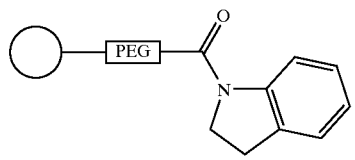

The resin alone was also tested to provide a background measurement. The screening protocol used was:
1. Weigh out approximately 1 mg of resin into an Eppendorf.
2. Incubate the resin with annealed rhodamine labelled double strand DNA for 24 hours at 37° C.
3. After 24 h incubation wash the resin 4 times and re-suspend beads in 50 mL of TE (EDTA and Tris buffer) or PBS (phosphate buffered saline).
4. Resin was transferred to a black 96 well plate with transparent base, fluorescence was measured from below at 635 nm using a Tecan Spectrofluor (590 nm excitation, 635 nm emission).

| Resin | Relative Fluorescence Units |
|---|---|
| TG Carboxy Resin | 892 |
| Indoline Bound to Resin | 625 |
| CBI Bound to Resin | 2947 |

Only a small amount of DNA binding was observed with the acid resin and with the resin loaded with an inactive indoline CBI mimic. An almost five fold differential was observed between the CBI resin and Indoline resin demonstrating DNA binding by the resin bound CBI. It is anticipated that a higher concentration of DNA would lead to a higher differential between the resins as it is possible that the CBI-resin is not saturated with DNA at this concentration.

EXAMPLE 6

Synthesis of a CBI-PED-hexapeptide Library
General Procedure for Acetylation/Endcapping After any coupling step the resin was treated with a mixture of pyridine (30%) and acetic anhydride (20%) in dichloromethane, to acetylate any free amine that has not been coupled to an amino acid. The formation of unexpected oligopeptides (carrying less than the expected number of aminoacids) is avoided.

The resin was treated with 3 mL of acetylating reagent and the slurry was agitated at room temperature for 1 hour. The reagents were then removed by filtration and the resin was rinsed with dichloromethane (2×5 mL) and methanol (2×5 mL).

General Procedure for Fmoc Deprotection

The resin was treated with 3 mL of a solution of piperidine (20%) in DMF. The mixture was then agitated for 2 hours at room temperature. The solvent was filtered off and the resin was rinsed with DMF (2×5 mL), dichloromethane (2×5 mL) and methanol (2×5 mL).

Fmoc-Glu-OAll Coupled to NovaSyn TG resin

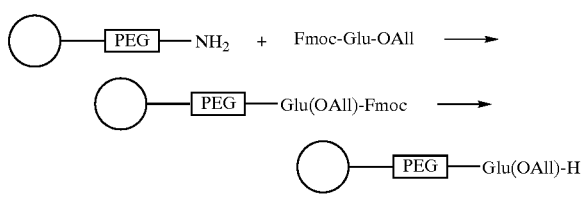

NovaSyn TG amino resin 130 μ (0.345 g, load 0.29 mmol/g, 0.1 mmol) was suspended ad swollen into 2 mL of DMF, under agitation (1000 rpm) for 30 minutes. The solvent was then removed and a solution of Fmoc-Glu-OAll (0.123 g, 0.3 mmol, 3 eq), TBTU (0.096 g, 0.3 mmol, 3 eq) and DIPEA (0.052 mL, 0.3 mmol, 3 eq) in 3 mL of DMF was added to the swollen resin. The resulting mixture was agitated at 1000 rpm, room temperature, overnight. The reaction mixture was filtered and the resin rinsed with DMF (2×2 mL), dichloromethane (2×5 mL) and methanol (2×5 mL).

The resin was then acetylated (see General procedure for acetylation) and deprotected (see General procedure for Fmoc deprotection).

HO-Gly-Fmoc Coupled to P-Glu (OAll)—H

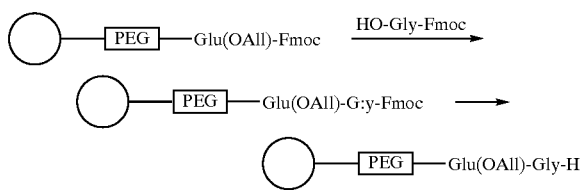

The resin was suspended in 2 mL of DMF and was allowed to swell for 30 minutes at room temperature, whilst being agitated (1000 rpm). DMF was removed and a solution of Fmoc-Gly-OH (0.089 g, 0.3 mmol, 3 eq), TBTU (0.096 g, 0.3 mmol, 3 eq) and DIPEA (0.052 mL, 0.3 mmol, 3 eq) in 3 mL of DMF was added to the resin. The mixture was shaken at room temperature for 12 hours. The reagents were then removed by filtration and the resin was rinsed with DMF (2×5 mL), dichloromethane (2×5 mL) and methanol (2×5 mL). The resin was then acetylated (see General procedure for acetylation) and deprotected (see General procedure for Fmoc deprotection) to afford the resin-bound dipeptide P-Glu (OAll)-Gly-H.

Split & Mix Procedure for the Resin Bound Hexadeptide P-Glu (OAll)-Gly-$X_1X_2X_3X_4$-H Sublibrary

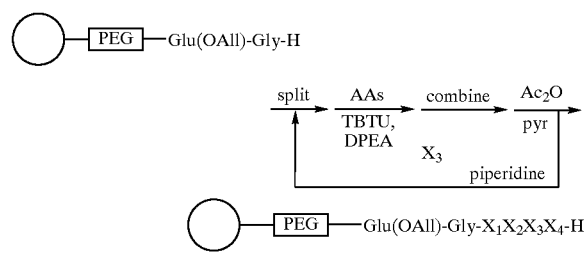

The resin was suspended in 3:1 mixture of 1,2-dichloroethane and DMF and equally partitioned into 17 4 mL Alltech tubes. Each tube thus contained 0.1/17 mmol= 5.88 $10^{-6}$ mol of resin-bound dipeptide. Solvent was removed in vacuo, and the resin was suspended in 200 mL of DMF and agitated for 30 minutes. The 17 aminoacids (1.76 $10^{-5}$ mmol, 3 eq for each step, 7.04 $10^{-5}$ mmol for 4 steps) were weighed into 17 vials:

| | | |
|---|---|---|
| 1. Fmoc-Ala-OH | | 22 mg |
| 2. Fmoc-Asn-OH | | 25 mg |
| 3. Fmoc-Asp(OtBu)-OH | | 29 mg |
| 4. Fmoc-Gln-OH | | 26 mg |
| 5. Fmoc-Glu(OtBu)-OH | | 30 mg |
| 6. Fmoc-Gly-OH | | 21 mg |
| 7. Fmoc-Ile-OH | | 25 mg |
| 8. Fmoc-Leu-OH | | 25 mg |
| 9. Fmoc-Lys(BOC)-OH | | 33 mg |
| 10. Fmoc-Met-OH | | 26 mg |
| 11. Fmoc-Phe-OH | | 27 mg |
| 12. Fmoc-Pro-OH | | 24 mg |
| 13. Fmoc-Ser(tBu)-OH | | 27 mg |
| 14. Fmoc-Thr(tBu)-OH | | 28 mg |
| 15. Fmoc-Trp(BOC)-OH | | 37 mg |
| 16. Fmoc-Tyr(tBu)-OH | | 32 mg |
| 17. Fmoc-Val-OH | | 24 mg |

Each amino acid was dissolved in 2 mL of DMF; 0.5 mL of this solution (corresponding to 1.76 $10^{-5}$ mmol, 3 eq of each amino acid) was added to the appropriate tube. TBTU (1.76 $10^{-5}$ mmol×17=2.99 $10^{-4}$, 96 mg) and DIPEA (1.76 $10^{-5}$ mmol×17=2.99 $10^{-4}$, 52 mL) were separately dissolved in 1.7 mL of DMF and each solution was evenly partitioned, addressing 3 eq of each reagent, to each one of the 17 tubes.

The reaction tubes were agitated at room temperature for 12 hours, then the reagents and solvents were removed in vacuo and the resin was rinsed with DMF (2×1 mL each tube), DCM (2×1 mL each tube) and methanol (2×1 mL each tube). The resin was then suspended in 3:1 mixture of 1,2-dichloroethane and DMF and recombined. The recombined resin was acetylated (3 mL of acetylating reagent, 1 hour, room temperature) and deprotected (3 mL of 20% piperidine in DMF, 2 hours, room temperature).

The procedure was repeated 3 more times to afford the deprotected resin-bound hexapeptide G (OAll) E$X_1X_2X_3X_4$H.

Coupling of Fmoc (Alloc) Lys-OH to Resin-Bound Hexapeptide

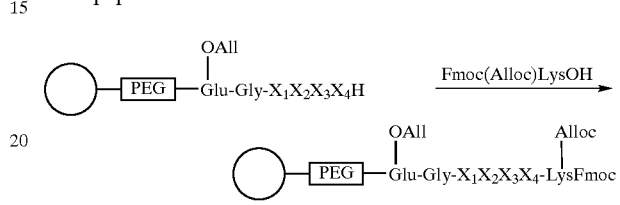

The resin was suspended in 2 mL of DMF and was allowed to swell for 10 minutes at room temperature, whilst being agitated (1000 rpm). DMF was removed and a solution of Fmoc (Alloc) Lys-OH (0.135 g, 0.3 mmol, 3 eq), TBTU (0.096 g, 0.3 mmol, 3 eq) and DIPEA (0.052 mL, 0.3 mmol, 3 eq) in 3 mL of DMF was added to the resin. The mixture was shaken at room temperature for 12 hours. The reagents were then removed by filtration and the resin was rinsed with DMF (2×5 mL), dichloromethane (2×5 mL) and methanol (2×5 mL). The resin was then acetylated (see General procedure for acetylation) to afford the resin-bound heptapeptide.

Deprotection of Allyl Ester

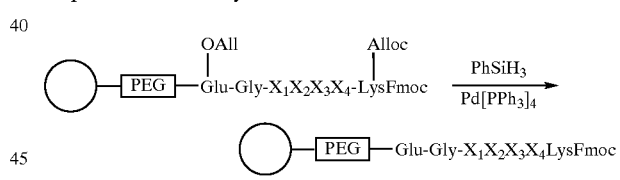

The resin was suspended in 2 mL of DCM. Phenylsilane (2.4 mmol, 24 eq, 0.29 mL) in 1 mL of DCM was added and the mixture was shaken at room temperature for 10 minutes. Pd[PPH$_3$]$_4$ (0.01 mmol, 0.1 eq, 11 mg) in 0.5 mL of DCM was added and the reaction mixture was shaken for further 10 minutes.

The reagents were filtered and the resin was rinsed with DCM (2×5 mL) and methanol (2×5 mL), then the procedure was repeated once again. The resin was finally dried under reduced pressure.

Coupling of N10-Fmoc Protected PBD to Lysine Residue of the Resin-Bound Heptapeptide

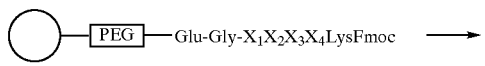

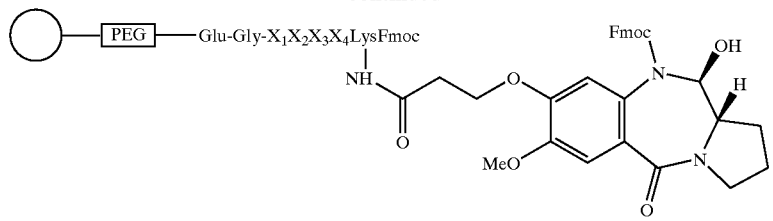

The resin was suspended in 2 mL of DMF and agitated for 10 minutes to allow swelling. DMF was then removed. A solution of N10-Fmoc-PBD acid (0.556 g, 1 mmol, 10 eq.), TBTU (0.353 g, 1.1 mmol, 1.1 eq.) and DIPEA (0.19 mL, 1.1 mmol, 1.1 eq.) in 3 mL of DMF was stirred for 30 minutes, and added to the resin. The mixture was agitated at room temperature for 12 hours, then the reagents were removed under reduced pressure and the resin was rinsed with DMF (2×5 mL), dichloromethane (2×5 mL), methanol (2×5 mL) and diethyl ether (1×2 mL).

Activation of Resin with 3-hydroxy-1,2,3-benzotriazin-4(3H)-one (HO-Dhbt)

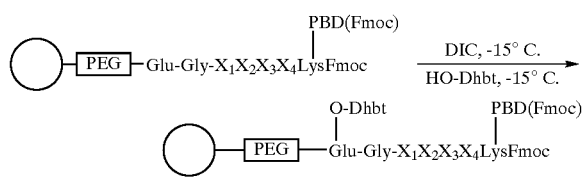

The resin was suspended and swollen in 2 mL of DMF for 10 minutes. DMF was removed and the resin was treated with 156 mL (1 mmol, 10 eq) of diisopropyl carbodiimide (DIC) in 2 mL of DMF. The resulting slurry was shaken for 15 minutes at −15° C. (acetone-ice bath), then washed with DMF (2×2 mL) the resin was re-suspended in 2 mL of DMF, cooled at −10° C. and treated with 163 mg (1 mmol, 10 eq) of HO-Dhbt. The mixture was shaken for 30 minutes at −10° C., for 4 hours at 0° C. and then allowed to stand at 0° C. overnight.

The reaction mixture was filtered and the resin washed with DMF (2×2 mL), dichloromethane (2×2 mL), MeOH (2×2 mL) and diethyl ether (2 mL). The activated resin was stored in freezer until ready for use.

Coupling of O-Dhbt Activated Resin with seco-CBI, in Presence of DIPEA

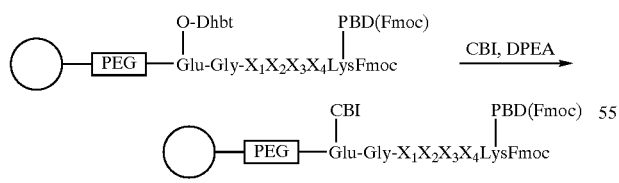

BOC-seco-CBI was deprotected immediately before coupling to the activated resin. 100 mg (0.3 mmol) of BOC-seco-CBI was dissolved in 15 mL of 3M HCl solution in anhydrous ethyl acetate. The mixture was cooled at 0° C. for 30 minutes and then allowed to warm to room temperature for further 30 minutes. TLC (4:1=petroleum ether:diethyl ether) revealed reaction completion; the reaction mixture was evaporated at reduced pressure and stored at −20° C.

O-Dhbt-activated resin was treated with seco-CBI dissolved in 2 mL of DMF and the mixture was shaken for 60 minutes at room temperature. At the end the reaction mixture was filtered and the resin was washed with DMF (2×2 mL), dichloromethane (2×2 mL), methanol (2×2 mL) and diethyl ether (2×1 mL). The resin was dried under reduced pressure and stored in a cool, dry place.

t-Butyl- and BOC-Deprotection on Side Chains

The resin was treated with a solution of TIS/TFA 2% in dichloromethane (2 mL). The mixture was shaken for 2 hours at room temperature. The reagents were removed in vacuo and the resin was rinsed with dichloromethane (2×5 mL) and methanol (2×5 mL).

Fmoc Deprotection

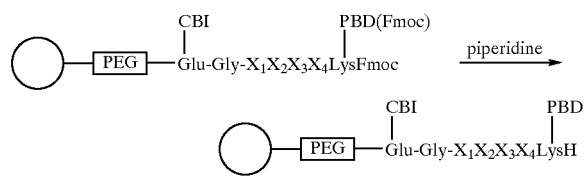

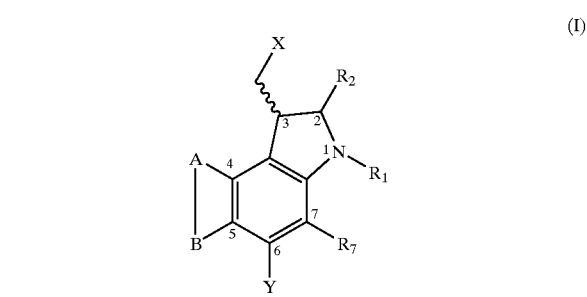

The resin was treated with 3 mL of a solution of piperidine (20%) in DMF, and agitated at room temperature for 2 hours. At the end the mixture was filtered and the resin was washed with DMF (2×5 mL), dichloromethane (2×5 mL) and methanol (2×5 mL). The resin was then dried under reduced pressure.

What is claimed is:

1. A compound of formula I capable of forming a combinatorial unit:

(I)

Wherein:

X is an electrophilic leaving group;

A and B collectively represent a fused benzene ring, which is substituted by a $CO_2H$ or $CO_2R$ group and is further optionally substituted by up to 3 groups independently selected from R, OH, OR, halo, nitro, amino, $Me_3Sn$, $CO_2H$, or $CO_2R$, wherein Y is selected from NH-Prot, O-Prot, S-Prot, $NO_2$, NHOH, $N_3$, NHR, NRR, N=NR, N(O)RR, $NHSO_2R$, N=NPHR, SR or SSR, where Prot represents a protecting group;

R₁ is a nitrogen protecting group, where if Y includes a protecting group, these protecting groups are orthogonal;

R₂ and R₇ are independently selected from H, R, OH, OR, halo, nitro, amino, or Me₃Sn;

wherein R is selected from:
(a) a lower alkyl group having 1 to 10 carbon atoms,
(b) an aralkyl group (i.e. an alkyl group with one or more aryl substituents), of up to 12 carbon atoms;
the alkyl group of (a) or (b) optionally containing one or more carbon—carbon double or triple bonds, which may form part of a conjugated system; and
(c) an aryl group, of up to 12 carbon atoms;

and wherein:
R is optionally substituted by one or more halo, hydroxy, amino, or nitro groups, and optionally contains one or more hetero atoms selected from the group consisting of sulfur and oxygen, which may form part of, or be, a functional group.

2. A compound according to claim 1, wherein R is independently selected from a lower alkyl group having 1 to 10 carbon atoms, or an aralkyl group, preferably of up to 12 carbon atoms, or an aryl group, preferably of up to 12 carbon atoms, optionally substituted by one or more halo, hydroxy, amino, or nitro groups.

3. A compound according to claim 2, wherein R is independently selected from lower alkyl groups having 1 to 10 carbon atoms optionally substituted by one or more halo, hydroxy, amino or nitro groups.

4. A compound according to claim 3, wherein R is an unsubstituted straight or branched chain alkyl group, having 1 to 10 carbon atoms.

5. A compound according to claim 1, wherein R₁ has a carbamate functionality where it binds to the nitrogen atom of the CPI.

6. A compound according to claim 1, wherein Y is NH-Prot, O-Prot or S-Prot.

7. A compound according to claim 6, wherein Y is NH-Prot.

8. A compound according to claim 1, wherein X is either halogen or OSO₂R.

9. A compound according to claim 1, wherein the 4,5 fused ring is substituted by —CO₂R in the 2 or 3 position.

10. A compound of the formula:

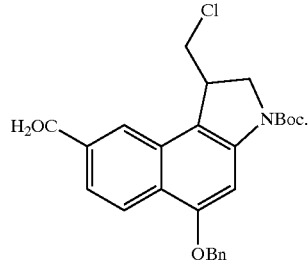

* * * * *

UNITED STATES PATENT AND TRADEMARK OFFICE
CERTIFICATE OF CORRECTION

PATENT NO. : 6,909,006 B1
DATED : June 21, 2005
INVENTOR(S) : David Edwin Thurston and Philip Wilson Howard It is certified that error appears in the above-identified patent and that said Letters Patent is hereby corrected as shown below:

Title page,
Item [22], PCT Filed, "Feb. 22, 2000" should read -- Aug. 24, 2000 --.

Signed and Sealed this

Twenty-third Day of August, 2005

JON W. DUDAS
*Director of the United States Patent and Trademark Office*